(12) United States Patent
Tanaka et al.

(10) Patent No.: US 12,285,306 B2
(45) Date of Patent: Apr. 29, 2025

(54) DENTAL HANDPIECE AND DENTAL HANDPIECE WITH CLEANING ADAPTER

(71) Applicant: NAKANISHI INC., Kanuma (JP)

(72) Inventors: Shinichi Tanaka, Kanuma (JP); Tomohiro Sakanushi, Kanuma (JP); Kohei Sekizuka, Kanuma (JP)

(73) Assignee: NAKANISHI INC., Kanuma (JP)

( * ) Notice: Subject to any disclaimer, the term of this patent is extended or adjusted under 35 U.S.C. 154(b) by 441 days.

(21) Appl. No.: 17/861,737

(22) Filed: Jul. 11, 2022

(65) Prior Publication Data

US 2023/0135224 A1    May 4, 2023

(30) Foreign Application Priority Data

Nov. 1, 2021 (JP) .................................. 2021-178835

(51) Int. Cl.
*A61C 17/22* (2006.01)
*A61C 17/02* (2006.01)
*A61C 17/20* (2006.01)

(52) U.S. Cl.
CPC ............ *A61C 17/225* (2013.01); *A61C 17/02* (2013.01); *A61C 17/20* (2013.01)

(58) Field of Classification Search
CPC .... A61B 2090/0813; A61C 1/07; A61C 17/20
See application file for complete search history.

(56) References Cited

U.S. PATENT DOCUMENTS

| 3,075,288 A | 1/1963 | Balamuth et al. |
| 3,427,480 A | 2/1969 | Robinson |
| RE30,536 E * | 3/1981 | Perdreaux, Jr. ........ A61C 17/20 433/119 |
| 5,395,240 A | 3/1995 | Paschke et al. |

(Continued)

FOREIGN PATENT DOCUMENTS

| AU | 2021102401 A4 | 7/2021 |
| GB | 1 602 496 A | 11/1981 |

(Continued)

OTHER PUBLICATIONS

Japanese Office Action dated Nov. 24, 2021, English translation included, 9 pages.

(Continued)

*Primary Examiner* — Cris L. Rodriguez
*Assistant Examiner* — Sydney J Pulvidente
(74) *Attorney, Agent, or Firm* — Rankin, Hill & Clark LLP

(57) ABSTRACT

A dental handpiece includes a cylindrical outer body, an insert body that includes an ultrasonic vibrator, and is accommodated in the outer body, a front end portion of the insert body and a rear end portion of the insert body, a tip connection portion that detachably holds a scale tip to which ultrasonic vibration from the ultrasonic vibrator is transmitted, and a cleaning liquid flow path that guides a cleaning liquid supplied from a cleaning liquid injection port of the insert body to a front end portion of the outer body. The cleaning liquid flow path includes an immersion flow path in (Continued)

which the insert body is immersed in the cleaning liquid in the outer body and the cleaning liquid in which the insert body is immersed is discharged from the front end portion of the outer body.

15 Claims, 20 Drawing Sheets

(56) References Cited

U.S. PATENT DOCUMENTS

| | | | | |
|---|---|---|---|---|
| 5,567,153 | A | * | 10/1996 | Foulkes .................. B23P 15/26 |
| | | | | 433/119 |
| 5,772,434 | A | | 6/1998 | Winston |
| 5,779,473 | A | * | 7/1998 | Sertich ................... A61C 17/20 |
| | | | | 366/126 |
| 5,853,290 | A | | 12/1998 | Winston |
| 6,175,580 | B1 | * | 1/2001 | Odaka ................ B23K 26/0096 |
| | | | | 372/33 |
| 2011/0033823 | A1 | * | 2/2011 | Gersh .................... A61C 17/20 |
| | | | | 433/119 |
| 2016/0088926 | A1 | * | 3/2016 | Jimenez ............... A46B 11/001 |
| | | | | 401/286 |
| 2019/0336161 | A1 | | 11/2019 | Scheller et al. |
| 2020/0093507 | A1 | * | 3/2020 | James ............ A61B 17/320068 |

FOREIGN PATENT DOCUMENTS

| | | |
|---|---|---|
| JP | 7-163585 | 6/1995 |
| JP | 10-503702 | 4/1998 |
| JP | 2004-351104 A | 12/2004 |
| JP | 2012-235979 | 12/2012 |
| WO | 2021/063309 A1 | 4/2021 |

OTHER PUBLICATIONS

European Search Report dated Jan. 4, 2023, European Application No. 22185912.7, 5 pages.
Japanese Office Action dated Nov. 24, 2021, Japanese Application No. 2021-178835, English translation included, 9 pages.

* cited by examiner

DENTAL HANDPIECE AND DENTAL HANDPIECE WITH CLEANING ADAPTER

CROSS REFERENCE TO RELATED APPLICATIONS

This application is based on Japanese Patent Applications No. 2021-178835 filed on Nov. 1, 2021, the entire contents of which are incorporated herein by reference.

TECHNICAL FIELD

The present disclosure relates to a dental handpiece and a dental handpiece with a cleaning adapter to which the cleaning adapter for supplying a cleaning liquid into the dental handpiece is connected.

BACKGROUND ART

There is known a dental handpiece for removing dental calculus and the like by using ultrasonic waves (for example, see JP-A-2012-235979). A dental handpiece disclosed in JP-A-2012-235979 includes an ultrasonic vibrator, a disinfectant flow path, a glass rod serving as an optical path for irradiating an affected area with light from a light source, and the like, and a scaler tip is attached to a tip end of the handpiece during treatment of a patient.

In a cleaning treatment including dental calculus removal, protein or the like contained in blood or saliva may splash and remain in a gap between the glass rod and a tip holding portion of the handpiece. Such residues are going to be treated in cleaning, disinfection, and sterilization processes of the dental handpiece after the treatment.

However, in the cleaning and sterilization processes described above, it is necessary to disassemble a part of the dental handpiece to facilitate treatment of the residues inside the handpiece, and an operation therefor is complicated.

Therefore, an object of the present disclosure is to provide a dental handpiece and a dental handpiece with a cleaning adapter, capable of sufficiently cleaning inside of the handpiece without disassembling the handpiece.

SUMMARY OF INVENTION

According to an aspect of t the present disclosure,
(1) A dental handpiece includes:
a cylindrical outer body;
an insert body that includes an ultrasonic vibrator, and is configured to be accommodated in the outer body, a front end portion of the insert body closing a front end of the outer body and a rear end portion of the insert body closing a rear end of the outer body;
a tip connection portion that is provided at the front end portion of the insert body and that detachably holds a scale tip to which ultrasonic vibration from the ultrasonic vibrator is transmitted; and
a cleaning liquid flow path that guides a cleaning liquid supplied from a cleaning liquid injection port of the insert body to a front end portion of the outer body,
wherein the cleaning liquid flow path includes an immersion flow path in which the insert body is immersed in the cleaning liquid in the outer body and the cleaning liquid in which the insert body is immersed is discharged from the front end portion of the outer body.
According to another aspect of the present disclosure,
(2) A dental handpiece with a cleaning adapter includes:
the dental handpiece according to (1); and
a cleaning adapter that is configured to be detachably connected to a rear end of the dental handpiece and guide the cleaning liquid supplied from an external device into the immersion flow path and the main body side water injection flow path.

DESCRIPTION OF EMBODIMENT

Figure 1:
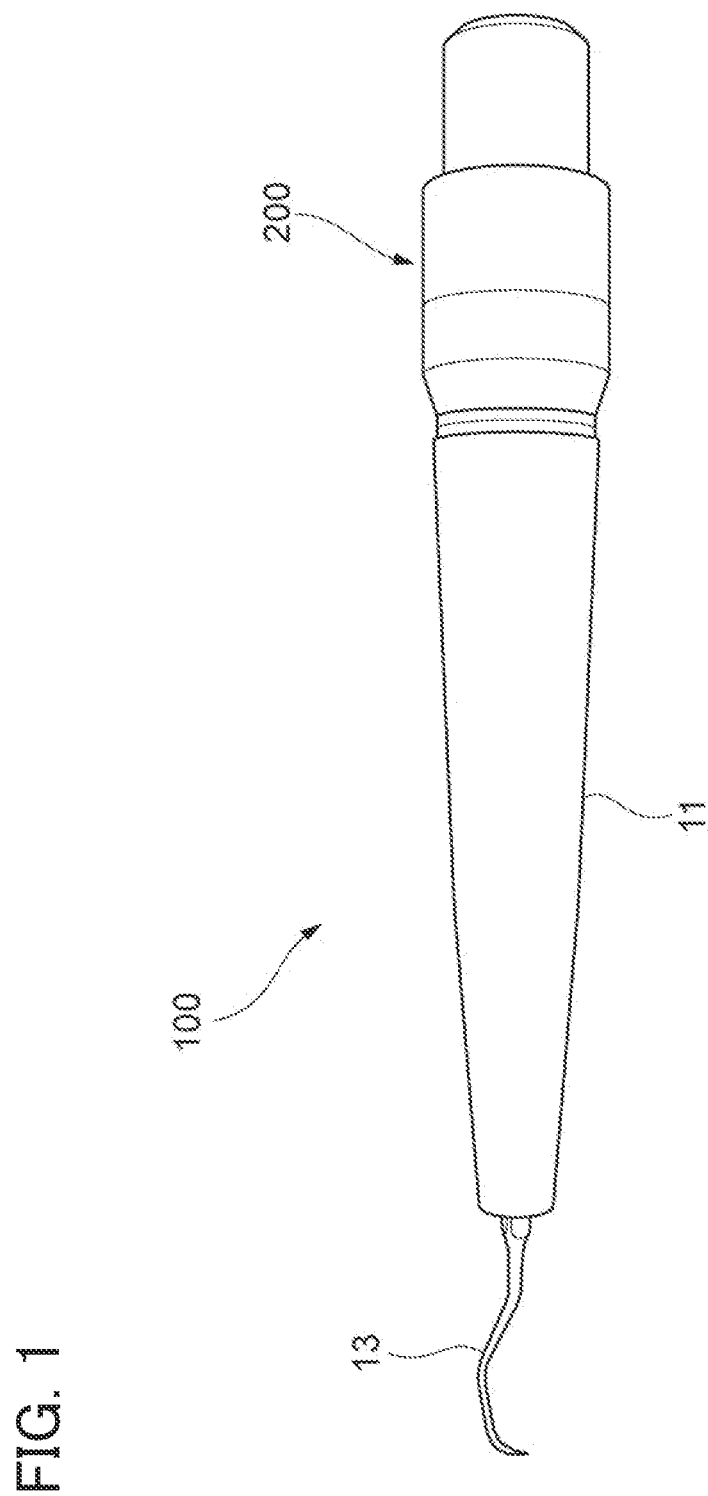
FIG. 1 is a side view showing an external appearance of a dental handpiece to which a scaler tip and a cleaning adapter are connected.

Hereinafter, an embodiment of a dental handpiece according to the present disclosure will be described in detail with reference to the drawings.
FIG. 1 is a side view showing an external appearance of a dental handpiece 100 to which a scaler tip 13 and a cleaning adapter 200 are connected.

The dental handpiece 100 includes a cylindrical outer body 11. The scaler tip 13 is detachably held at a front end portion of the outer body 11, and the cleaning adapter 200 to be described in detail later is connectable to a rear end portion of the outer body 11.

In the present specification, a connection side of the scaler tip 13 to the dental handpiece 100 is referred to as "forward", a "front end side", and "front", a connection side of the cleaning adapter 200 thereto is referred to as "rear" and a "rear end side", and a longitudinal direction of the dental handpiece 100 is referred to as an "axial direction".

<Configuration of Dental Handpiece>

Figure 2:
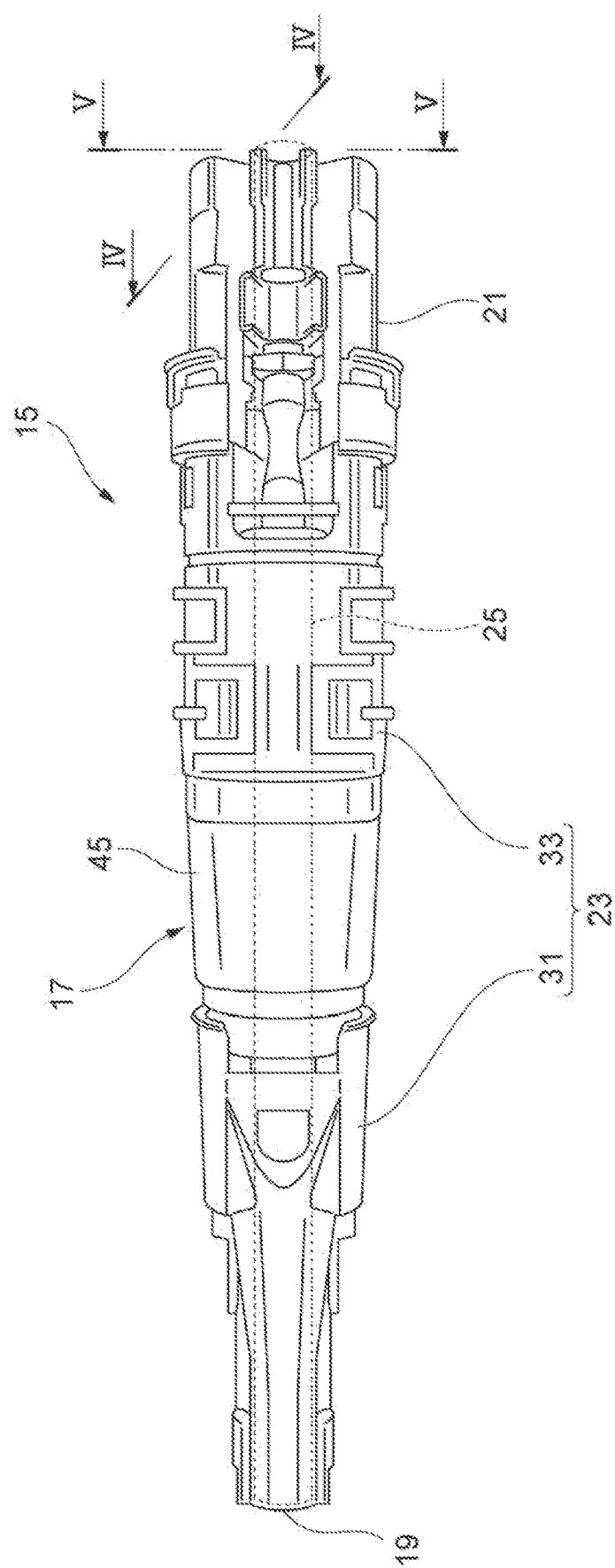
FIG. 2 is a schematic side view of an insert body.

FIG. 2 is a schematic side view of an insert body 15.

Figure 3:
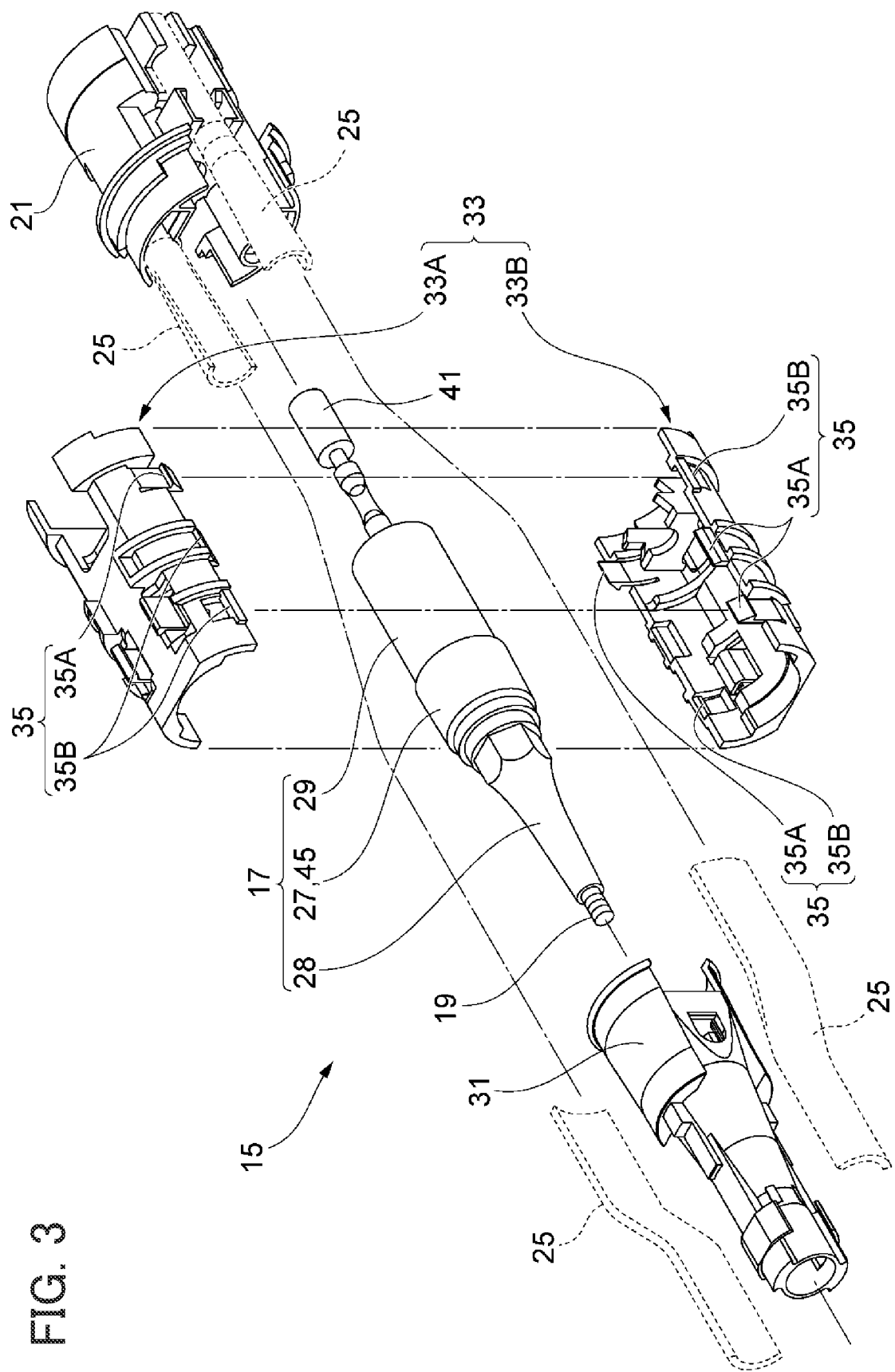
FIG. 3 is a schematic exploded perspective view of the insert body.

The insert body 15 is accommodated in the outer body 11 of the dental handpiece 100. FIG. 3 is a schematic exploded perspective view of the insert body 15. A shape of each member shown here is an example for explaining the embodiment, and the present disclosure is not limited thereto.

As shown in FIG. 2, the insert body 15 includes an ultrasonic vibrator 17 and a tip connection portion 19 provided at a front end portion thereof, and a cleaning liquid injection port to be described later is provided at a rear end portion thereof. In this configuration, the cleaning liquid injection port is provided in a connector portion 21 of the insert body 15, which is connected to a hose or a cleaning device connected to a handpiece control device (not shown). The front end portion of the insert body 15 closes a front end of the outer body 11, and the rear end portion of the insert body 15 closes a rear end of the outer body 11, whereby the insert body 15 seals an internal space of the outer body 11. A housing portion 23 that covers a front end side and a rear end side of the ultrasonic vibrator 17 is provided outside the ultrasonic vibrator 17. A pair of glass rods 25 (only a front side is indicated by a dotted line in FIG. 2) are disposed along an axial direction of the insert body 15 outside the housing portion 23. The glass rod 25 guides laser light or the like supplied from an optical connector (not shown) connected to the connector portion 21 to the front end portion of the insert body 15. The dental handpiece 100 may not include the glass rod 25.

As shown in FIG. 3, the ultrasonic vibrator 17 includes an ultrasonic vibration source 27 that generates ultrasonic vibration, a front horn 28, and a rear horn 29. The front horn 28 is a vibration transmission member that is connected to a front end side of the ultrasonic vibration source 27 and transmits the generated ultrasonic vibration to the scaler tip 13 (FIG. 1), and a front end of the front horn 28 serves as the tip connection portion 19. The rear horn 29 is connected to a rear end side of the ultrasonic vibration source 27.

The housing portion 23 includes a front end side collar 31 that covers a region from the ultrasonic vibration source 27 to the front end of the front horn 28, and a rear end side collar 33 that covers a region from the ultrasonic vibration source 27 to a rear end of the rear horn 29. The rear end side collar 33 is preferably formed of a pair of collar half bodies 33A, 33B each having a half cylindrical shape. In this case, the pair of collar half bodies 33A, 33B include engagement portions 35 that engage with each other in a case where the pair of collar half bodies 33A, 33B are combined with each other. In the engagement portions 35, a claw portion 35A provided on one of the collar half bodies 33A, 33B is engaged with a receiving portion 35B provided on the other of the collar half bodies 33A, 33B, whereby the collar half bodies 33A, 33B are integrally combined. The collar half body 33A and the collar half body 33B have the same shape, and the claw portion 35A and the receiving portion 35B are engaged with the corresponding receiving portion 35B and claw portion 35A, respectively. Only the rear end side collar 33 is limited to the half cylindrical shape, and the front end side collar 31 may have a half cylindrical shape, or both may have a half cylindrical shape.

Figure 4:
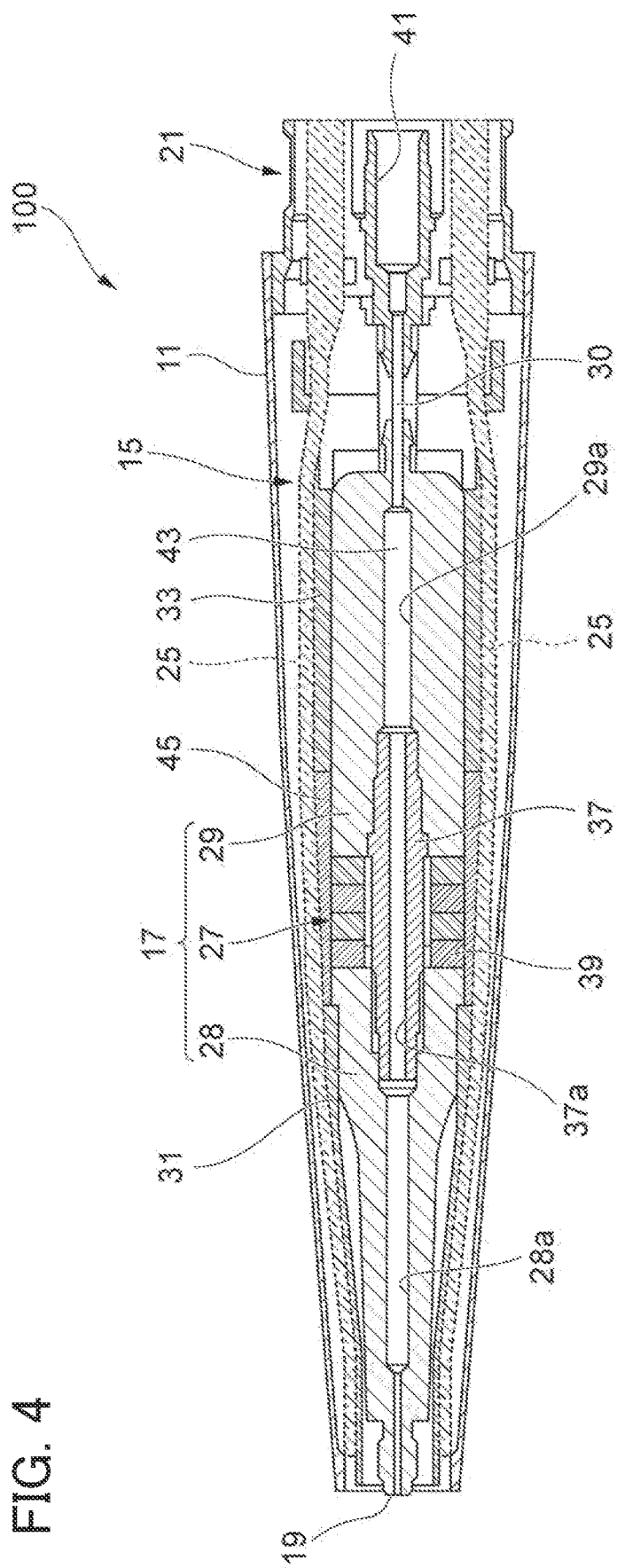
FIG. 4 is a schematic cross-sectional view taken along a line IV-IV in FIG. 2.
Figure 5:
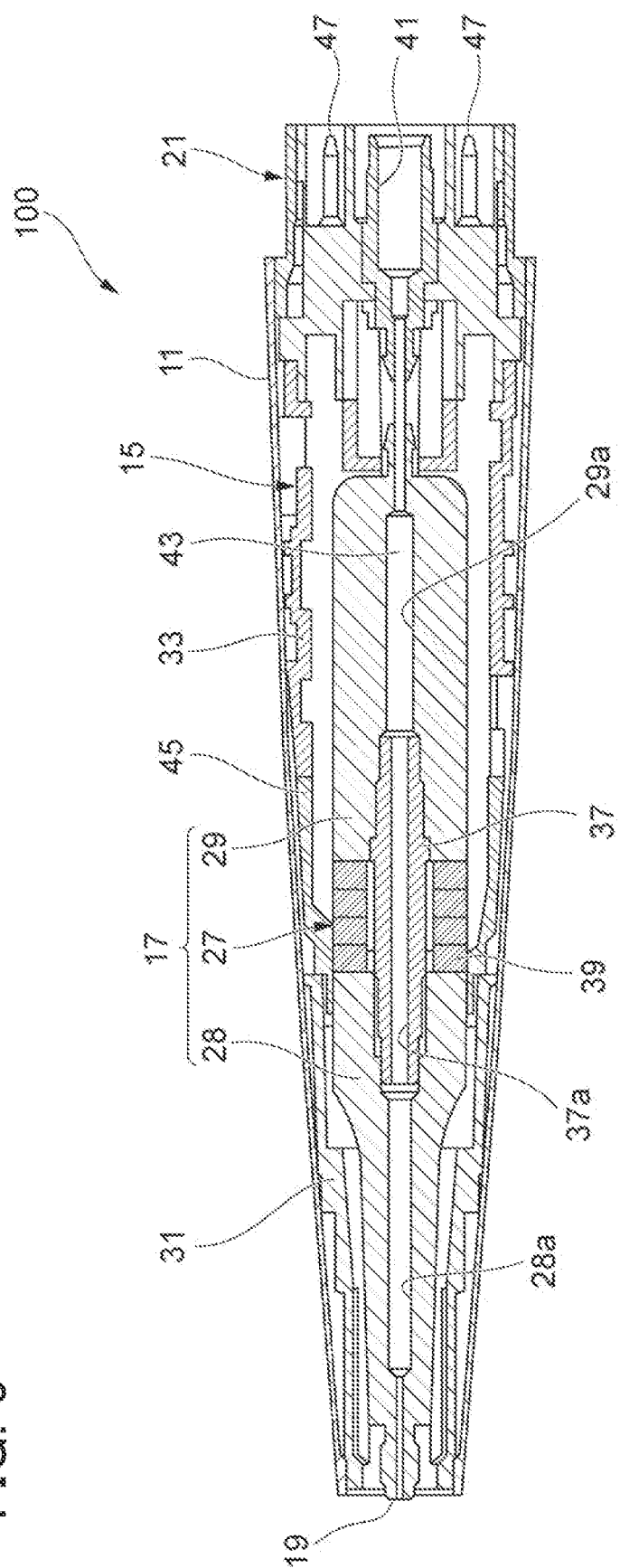
FIG. 5 is a schematic cross-sectional view taken along a line V-V in FIG. 2.

FIG. 4 is a schematic cross-sectional view taken along a line IV-IV in FIG. 2. FIG. 5 is a schematic cross-sectional view taken along a line V-V in FIG. 2 (also see FIG. 6 to be described later for the line IV-IV and the line V-V). In the following description, the same members or portions are denoted by the same reference numerals, and description thereof will be simplified or omitted.

As shown in FIGS. 4 and 5, the front horn 28 and the rear horn 29 of the ultrasonic vibrator 17 are connected to each other via a connection member 37, and a vibrating body 39 is disposed on an outer periphery of the connection member 37. The front horn 28, the connection member 37, and the rear horn 29 respectively have through holes 28a, 37a, 29a penetrating in the axial direction. The through holes 28a, 37a, 29a and a connection flow path 30 that allows a central connection port 41 of the connector portion 21 to communicate with the rear horn 29 form a main body side water injection flow path 43. The main body side water injection flow path 43 is formed so as to penetrate a central axis of the insert body 15 from the central connection port 41 to the tip connection portion 19, and is used for water supply to an affected area or the like during treatment of a patient.

An outer periphery of the ultrasonic vibration source 27 is liquid-tightly covered with an elastic cover 45 made of silicon rubber or the like having insulating properties and chemical resistance. A cable (not shown) connected to an electrode terminal 47 shown in FIG. 5 is connected to the vibrating body 39.

Figure 6:
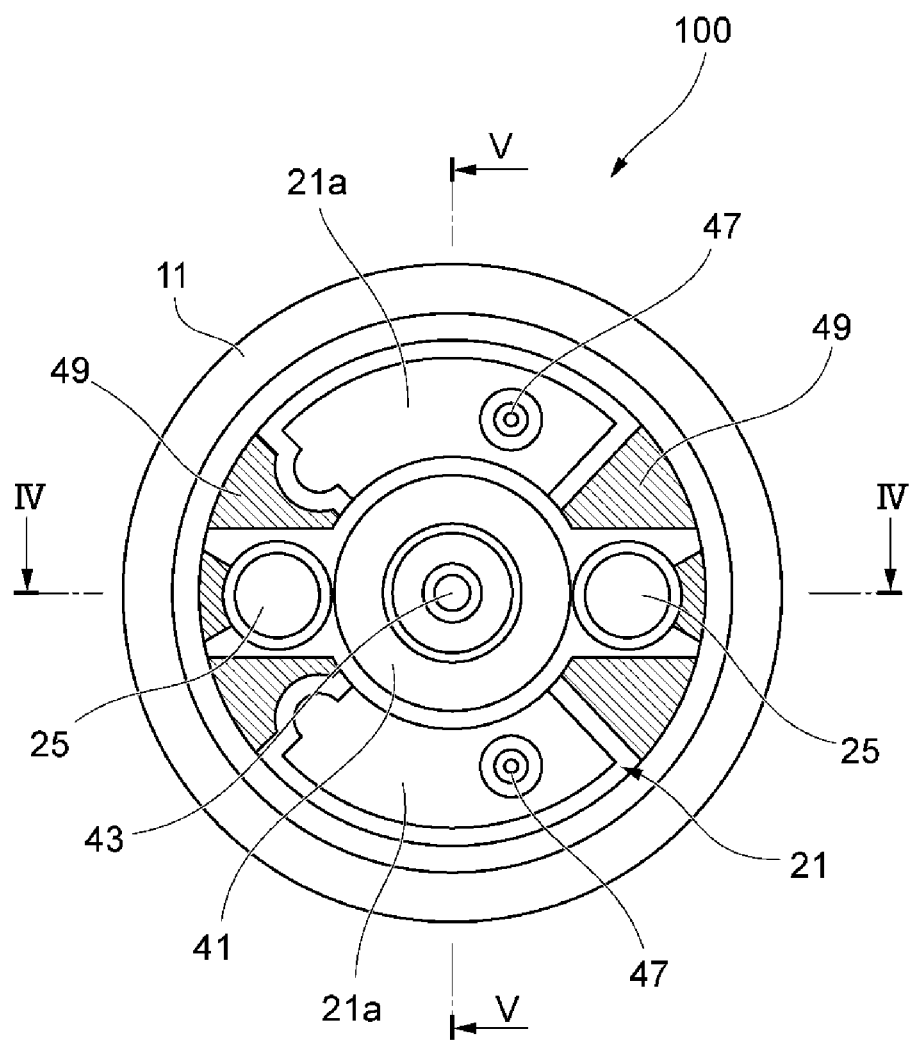
FIG. 6 is an end view of a rear end side of the dental handpiece.

FIG. 6 is an end view of a rear end side of the dental handpiece 100.

As shown in FIG. 6, the central connection port 41 is disposed on a central axis of the connector portion 21. Liquid may be sent from the central connection port 41 to the main body side water injection flow path 43. A pair of electrode terminals 47 are disposed in a bottomed recess 21a of the connector portion 21. End portions of the pair of glass rods 25 are fixed to the connector portion 21 so as to be disposed on both sides of the central connection port 41.

A gap in a circumferential direction between the glass rod 25 and the bottomed recess 21a in the connector portion 21 is a cleaning liquid injection port 49 (indicated by hatching in FIG. 6) for injecting a cleaning liquid to be described later. At the rear end of the outer body 11, only the cleaning liquid injection port 49 of the connector portion 21 communicates with inside of the outer body 11, and the other portions have an airtight and watertight structure. That is, gas and liquid do not enter the inside of the outer body 11 from a portion other than the cleaning liquid injection port 49.

Figure 7:
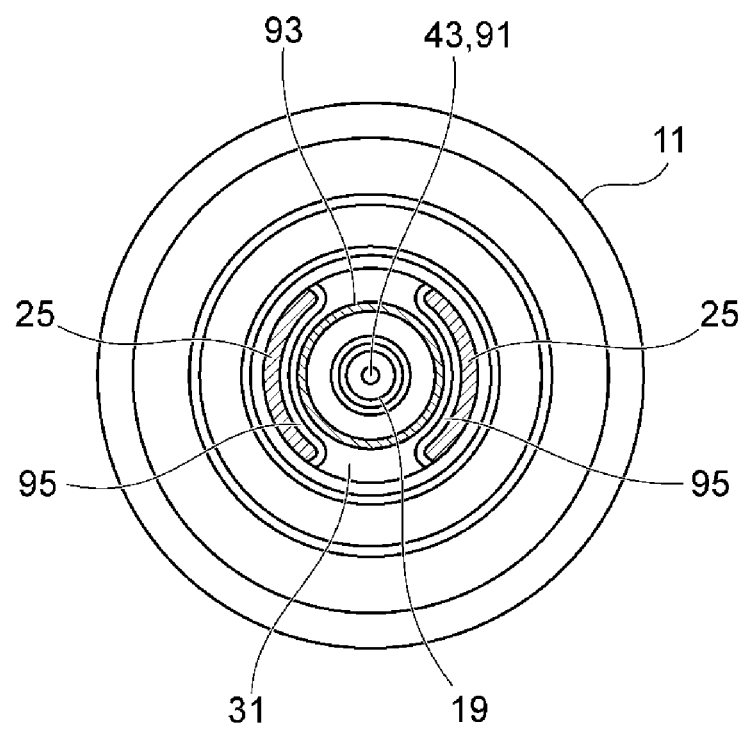
FIG. 7 is an end view of a front end side of the dental handpiece.

FIG. 7 is an end view of a front end side of the dental handpiece 100.

As shown in FIG. 7, a discharge port 91 of the main body side water injection flow path 43 is provided in a center of the tip connection portion 19. Light emitting ends of the pair of glass rods 25 are fixed to the front end side collar 31 on an outer side of the tip connection portion 19. An annular gap between the tip connection portion 19 and the front end side collar 31 is a cleaning liquid discharge port 93 to be described in detail later, and an arc-shaped gap between the glass rod 25 and the front end side collar 31 is a cleaning liquid discharge port 95 to be described in detail later. In a case where the dental handpiece 100 does not include the glass rod 25, a light emitting end of the front end side collar 31 is sealed together with the discharge port 95, and the cleaning liquid is discharged from the discharge ports 91, 95

<Cleaning Liquid Flow Path>

Next, a flow path of the cleaning liquid that cleans inside of the dental handpiece 100 having the above configuration will be described.

Figure 8:
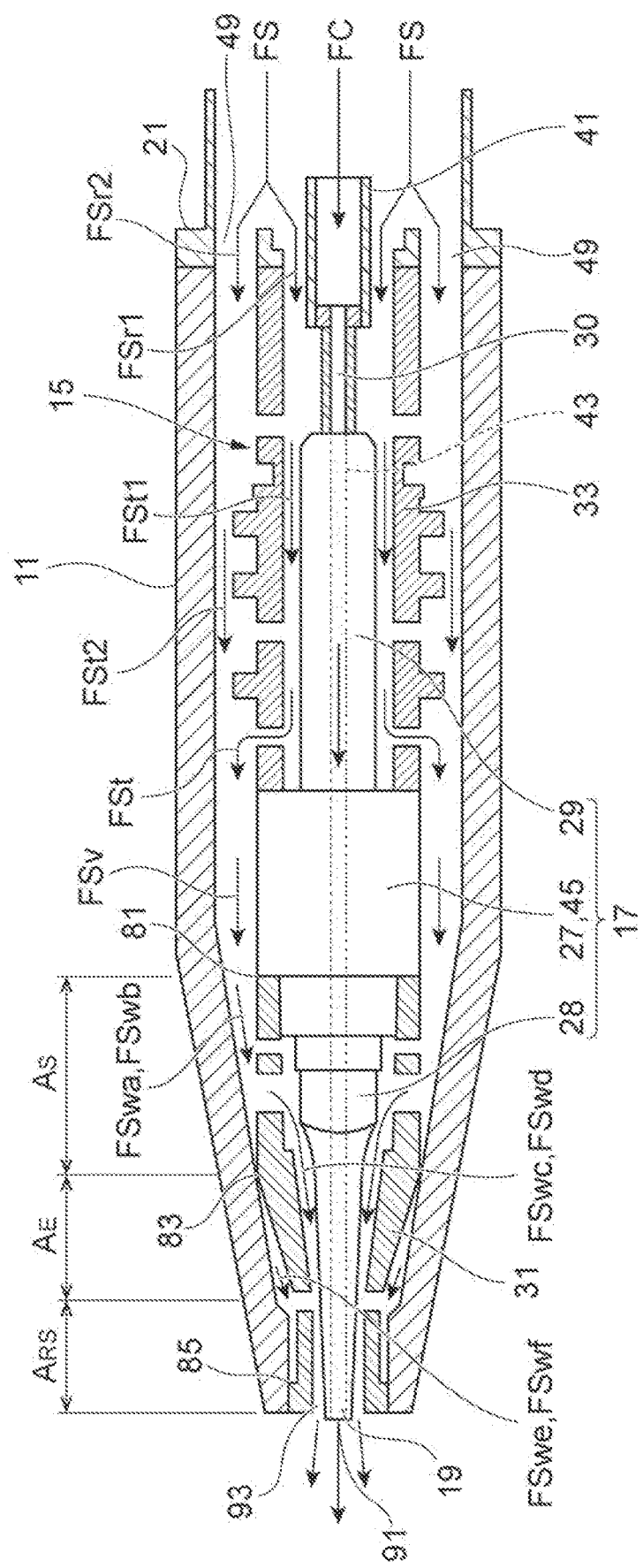
FIG. 8 is an explanatory view schematically showing an internal structure of the dental handpiece and a flow path of a cleaning liquid.

FIG. 8 is an explanatory view schematically showing an internal structure of the dental handpiece 100 and the flow path of the cleaning liquid.

As shown in FIG. 8, the flow path through which the cleaning liquid is supplied from the connector part 21 into the handpiece includes a central flow path FC through which the cleaning liquid is supplied from the central connection port 41 and a peripheral flow path FS through which the cleaning liquid is supplied from the cleaning liquid injection port 49. The cleaning liquid supplied to the central flow path FC is sent from the central connection port 41 to the tip connection portion 19 through the main body side water injection flow path 43. Thereby, the main body side water injection flow path 43 is cleaned.

The cleaning liquid supplied to the peripheral flow path FS is an in-case immersion flow path in which the insert body 15 is immersed in the cleaning liquid in the outer body 11 and the cleaning liquid in which the insert body 15 is immersed is discharged from a front end portion of the outer body. The peripheral flow path FS is divided into an inner flow path FSr1 passing through a center side close to the central connection port 41 and an outer flow path FSr2 passing through a outer body 11 side during flowing through the connector portion 21.

Figure 9A:
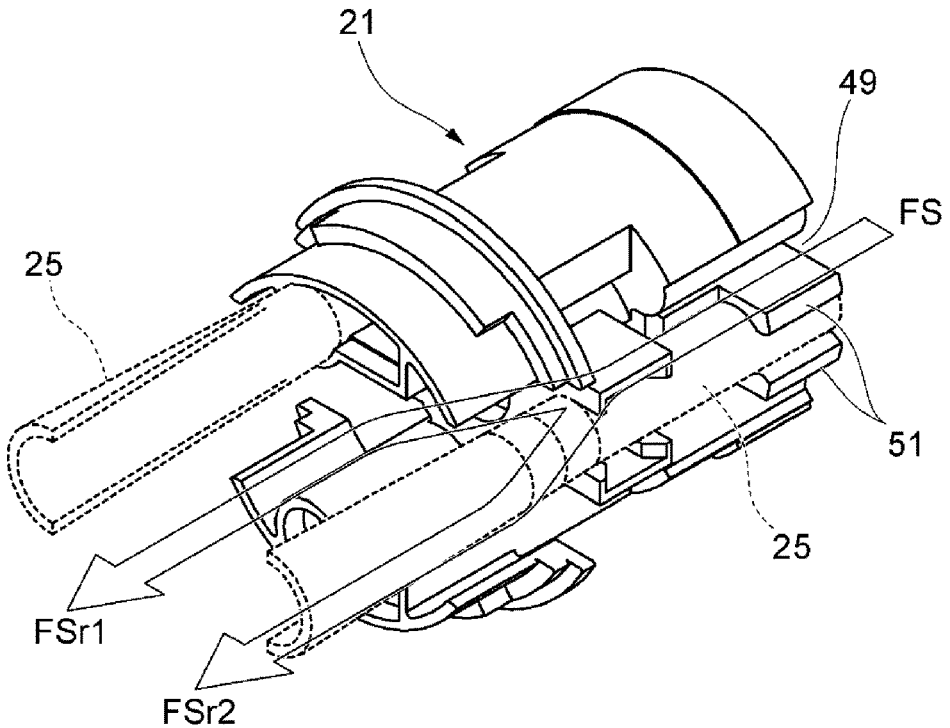
FIG. 9A is a schematic perspective view showing a flow path of the cleaning liquid formed in a connector portion.
Figure 9B:
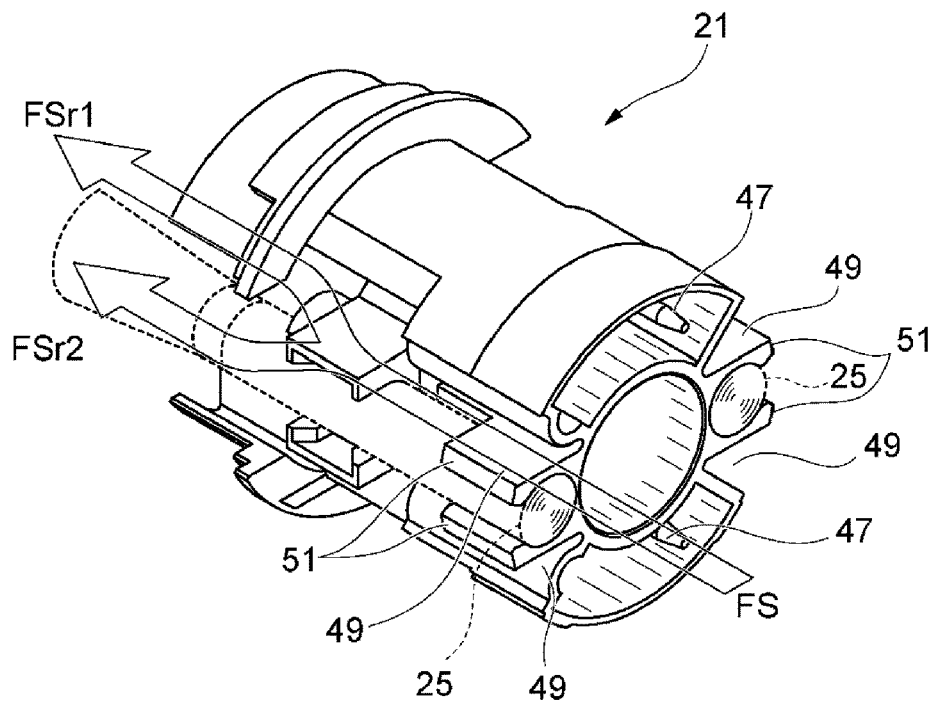
FIG. 9B is a schematic perspective view showing the flow path of the cleaning liquid formed in the connector portion.

FIGS. 9A and 9B are schematic perspective views showing the flow path of the cleaning liquid formed in the connector portion 21. FIGS. 9A and 9B representatively show the flow path of a part of the cleaning liquid supplied from a pair of cleaning liquid injection ports 49.

As shown in FIGS. 9A and 9B, the cleaning liquid supplied from the cleaning liquid injection port 49 flows forward in the flow path while being stirred by unevenness formed by the glass rods 25, glass rod rear end holding portions 51 that fix the glass rods 25 by a snap-fit structure, and the like. The connector portion 21 is connected to the rear end side collar 33 in the outer body 11 shown in FIG. 8, and the inner flow path FSr1 and the outer flow path FSr2 each extend to the front end side along an axial direction of the rear end side collar 33 and become an inner flow path FSt1 and an outer flow path FSt2 to be described later. Although the connector portion 21 is formed separately from the rear end side collar 33, the present disclosure is not limited thereto, and the connector portion 21 may be formed integrally with the rear end side collar 33.

Figure 10A:
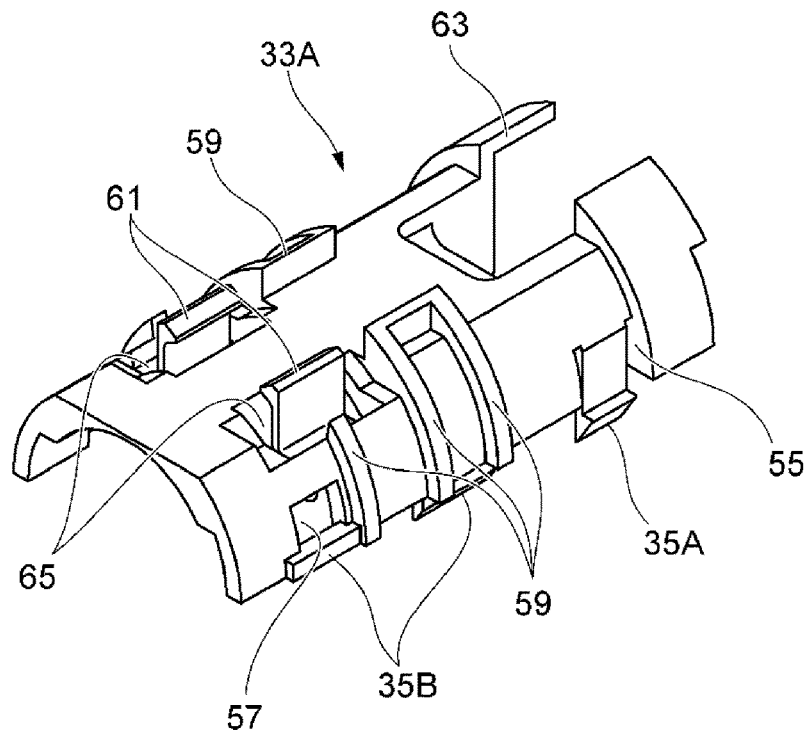
FIG. 10A is a schematic perspective view of one collar half body of a rear end side collar.
Figure 10B:
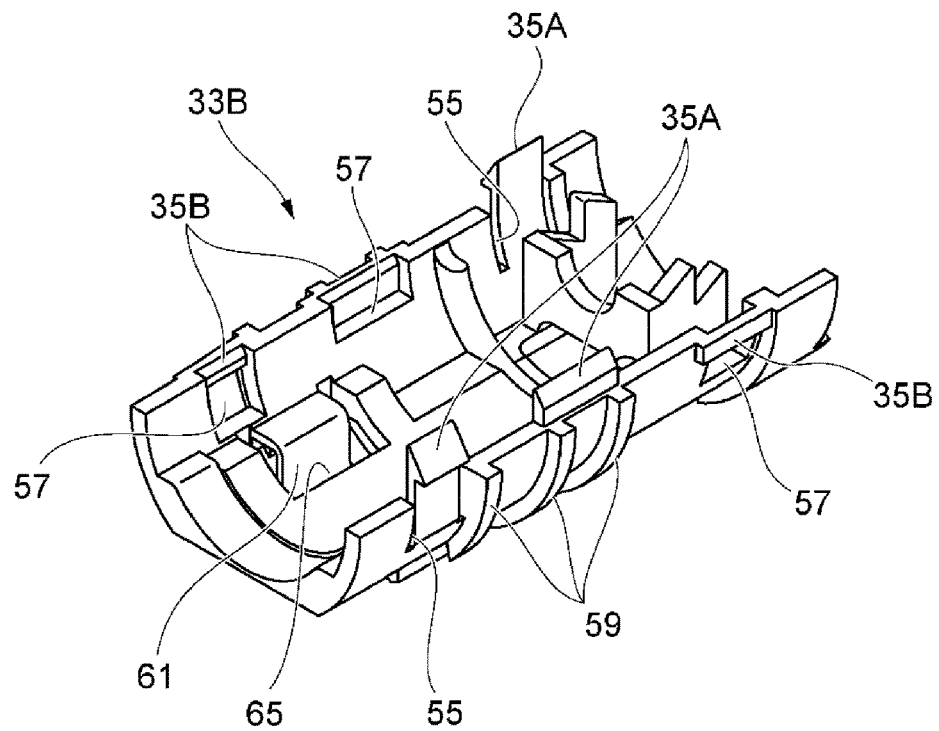
FIG. 10B is a schematic perspective view of the other collar half body of the rear end side collar.

FIG. 10A is a schematic perspective view of one collar half body 33A of the rear end side collar 33. FIG. 10B is a schematic perspective view of the other collar half body 33B of the rear end side collar 33.

As shown in FIGS. 10A and 10B, a pair of collar half bodies 33A, 33B constituting the rear end side collar 33 has a plurality of claw portions 35A and receiving portions 35B that engage with each other. The claw portion 35A may be a protruding piece defined by a slit formed on the collar half bodies 33A, 33B, or a protruding piece formed by protruding from a part of the collar half bodies 33A, 33B.

The slit formed around the claw portion 35A in the hollowed state is a through hole 55 penetrating the collar half bodies 33A, 33B in a thickness direction. The receiving portion 35B is provided with a through hole 57 into which a tip end portion of the claw portion 35A is inserted. A protrusion 59 including a rib protruding in the thickness direction and various grooves recessed in the thickness direction are formed on outer peripheral surfaces of the collar half bodies 33A, 33B. Glass rod holding portions 61 that fix the glass rods by a snap-fit structure and a notch 63 are also formed, and a through hole 65 is formed around the glass rod holding portion 61. In this way, the rear end side collar 33 is provided with a large number of through holes 55, 57, 65, the protrusion 59, the notch 63, and recesses including the grooves.

In a region of the rear end side collar 33 shown in FIG. 8, the cleaning liquid flows toward the front end side along the inner flow path FSt1 flowing on an inner peripheral side of the rear end side collar 33 and the outer flow path FSt2 passing through a space between an outer peripheral side of the rear end side collar 33 and the outer body 11.

Figure 11:
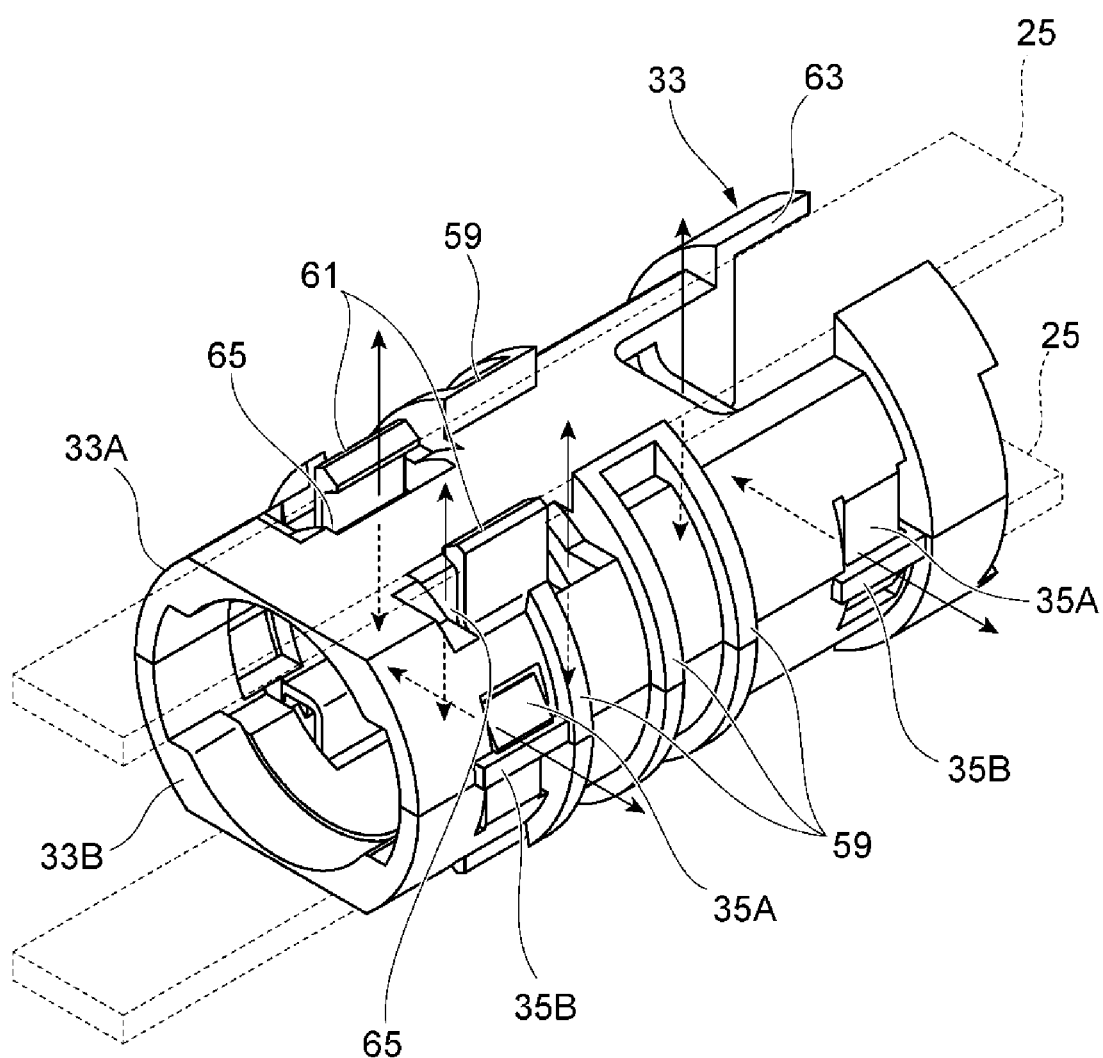
FIG. 11 is a schematic perspective view of the rear end side collar in which collar half bodies are combined.

FIG. 11 is a schematic perspective view of the rear end side collar 33 in which the collar half bodies 33A, 33B are combined.

During passage of the cleaning liquid through the region of the rear end side collar 33, as indicated by arrows in FIG. 11, the cleaning liquid flows from the inner flow path FSt1 to the outer flow path FSt2 or from the outer flow path FSt2 to the inner flow path FSt1 through through holes formed in the rear end side collar 33, and diffusion of the cleaning liquid is promoted. An effect of stirring the cleaning liquid is enhanced by unevenness formed in the rear end side collar 33.

Even in a case where the glass rod 25 indicated by a dotted line in FIG. 11 is assembled, the cleaning liquid is stirred while changing a flow direction in a gap between the glass rod 25 and the rear end side collar 33 and a gap between the rear end side collar 33 and an inner peripheral surface of the outer body 11 (not shown).

The cleaning liquid flowing through the inner flow path FSt1 is guided to the outer flow path FSt2 through a through hole as indicated by an arrow FSt on a connection end side of the rear end side collar 33 with the ultrasonic vibration source 27. Then, the cleaning liquid in which the cleaning liquid from the inner flow path FSt1 of the rear end side collar 33 and the cleaning liquid from the outer flow path FSt2 merge with each other becomes a flow path FSv flowing outside the ultrasonic vibration source 27, that is, outside the elastic cover 45 shown in FIG. 8, and is directed toward the front end side collar 31.

Figure 12A:
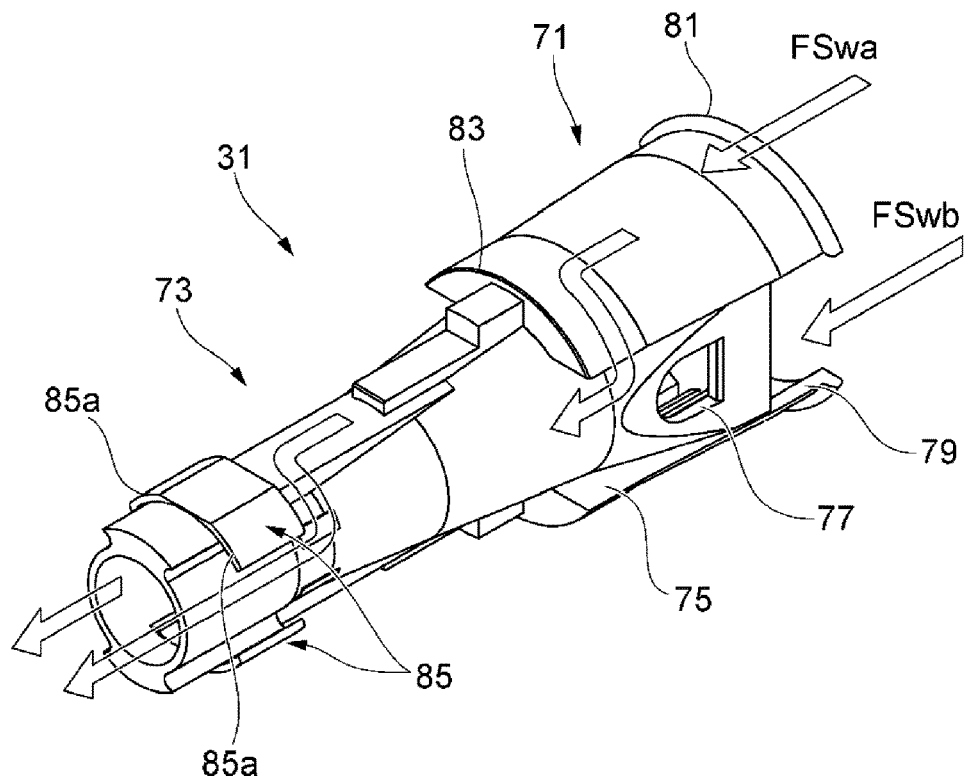
FIG. 12A is a schematic perspective view of a front end side collar as viewed from the front end side.
Figure 12B:
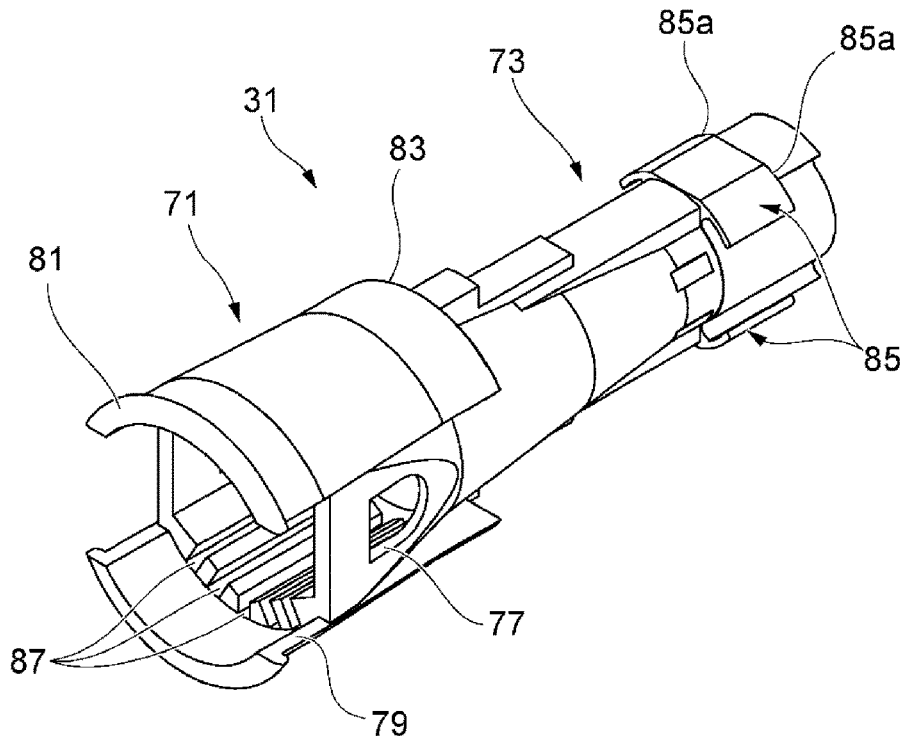
FIG. 12B is a schematic perspective view of the front end side collar as viewed from the rear end side.

FIG. 12A is a schematic perspective view of the front end side collar 31 as viewed from the front end side. FIG. 12B is a schematic perspective view of the front end side collar 31 as viewed from the rear end side.

The front end side collar 31 includes a large diameter portion 71 on the rear end side and a small diameter portion 73 extending from the large diameter portion 71 to the front end side. Substantially half of the large diameter portion 71 in the circumferential direction is formed in a cylindrical shape, and a remaining substantially half of the large diameter portion 71 is formed as a pair of notches 75 that accommodate the glass rods 25 (not shown). The pair of notches 75 are formed to face each other in a radial direction. Opening holes 77, 79 communicating with an inner space of the cylindrical large diameter portion 71 are formed in a bottom portion of the notch 75 on a radially inner side. A flange portion 81 facing the ultrasonic vibration source 27 is provided at a rear end of the large diameter portion 71, and an edge portion 83 abutting on the inner peripheral surface of the outer body 11 is provided at a front end of the large diameter portion 71. As shown in FIG. 12B, slit grooves 87 extending in the axial direction are formed in an inner peripheral surface of the cylindrical large diameter portion 71.

The small diameter portion 73 has a multistage, substantially cylindrical shape whose diameter decreases toward the front end side, and glass rod front end holding portions 85 that fix the glass rods 25 by a snap-fit structure are provided at a front end portion of the small diameter portion 73 so as to correspond to the pair of notches 75. The glass rod front end holding portions 85 are provided so as to protrude radially outward from an outer peripheral surface of the small diameter portion 73, and are in contact with the inner peripheral surface of the outer body 11 (not shown).

In the front end side collar 31, a flow path reduction portion $A_S$ in which a flow path cross-sectional area of an outer flow path gradually decreases is formed from the flange portion 81 to the edge portion 83 shown in FIG. 8. In the flow path reduction portion $A_S$, the cleaning liquid flowing through the outer flow path is divided into an inner flow path and an outer flow path of the front end side collar 31.

As shown in FIG. 12A, the cleaning liquid from the outer flow path FSv reaching the front end side collar 31 flows along a flow path FSwa flowing forward over the flange portion 81 and a flow path FSwb flowing forward through a gap between the outer body 11 and the front end side collar 31 at a position where the glass rod 25 (not shown) is held between the notch 75.

Figure 13:
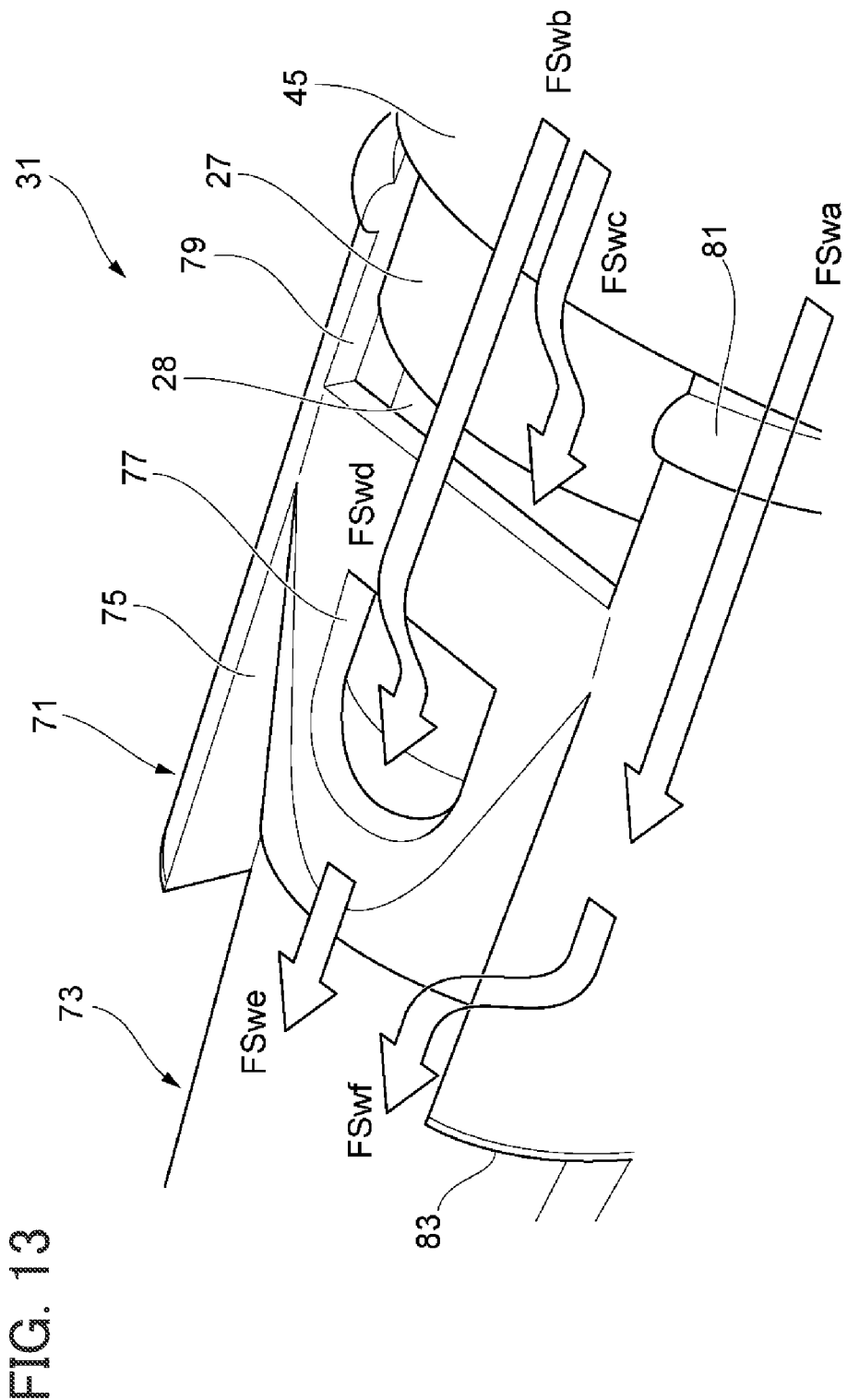
FIG. 13 is an explanatory view showing a flow of the cleaning liquid in the front end side collar.

FIG. 13 is an explanatory view showing a flow of the cleaning liquid in the front end side collar 31.

A flow of the flow path FSwb is mainly divided into a flow path FSwc that flows into inside of the front end side collar 31 from the opening hole 79 that opens to the notch 75 of the large diameter portion 71, a flow path FSwd that flows into the inside of the front end side collar 31 from the opening hole 77, and a flow path FSwe that leads to outside of the small diameter portion 73 over the opening holes 77, 79. The cleaning liquid in the flow path FSwc flows forward inside the front end side collar 31 while being rectified along the slit grooves 87 shown in FIG. 12B. The cleaning liquid in the flow path FSwd also merges with the flow path FSwc inside the front end side collar 31 and flows forward.

On the other hand, since an outer flow path of the flow path FSwa is closed by the edge portion 83 of the large diameter portion 71, the flow path FSwa becomes a flow path FSwf extending from the notch 75 toward an outer periphery of the small diameter portion 73, merges with the flow path FSwe, and flows outside the front end side collar 31.

A connection portion of the small diameter portion 73 with the large diameter portion 71 has a tapered shape whose outer diameter gradually decreases. Thereby, as shown in FIG. 8, an outer flow path ahead of the edge portion 83 becomes a flow path enlargement portion $A_E$ in which a flow path cross-sectional area gradually increases. In the flow path enlargement portion $A_E$, since a flow path width is narrowed by the edge portion 83 and then widened, changes in a flow direction and a flow velocity of the cleaning liquid become large, and stirring of the cleaning liquid is promoted.

Then, as shown in FIG. 12A, at a front end portion of the front end side collar 31, the flow path cross-sectional area of the outer flow path is narrowed by the glass rod front end holding portions 85, and at front end edges 85a of the glass rod front end holding portions 85, the front end edges 85a come into contact with the inner peripheral surface of the outer body 11 and a part of the outer flow path in the circumferential direction is closed. Thereby, in the outer flow path, the flow of the cleaning liquid is concentrated on the glass rod front end holding portions 85. In this way, a portion closer to the front end side than the flow path enlargement portion $A_E$ shown in FIG. 8 is a re-reduction portion $A_{RS}$ in which the flow path cross-sectional area of the outer flow path gradually decreases again. The re-reduction portion $A_{RS}$ is an outer flow path regulation portion, and regulates a part of the cleaning liquid in the outer flow path passing through the re-reduction portion $A_{RS}$. Thereby, the cleaning liquid is stirred in a turbulent flow and discharged from a discharge port of the outer flow path. The inner flow path of the front end side collar 31 is connected to a periphery of the tip connection portion 19 of the front horn 28 through a space between the front end side collar 31 and an outer peripheral surface of the front horn 28.

As a result, a front end of the dental handpiece 100 shown in FIG. 7 is provided with the discharge port 91 of the main body side water injection flow path 43 opened at a center of the tip connection portion 19, the discharge port 93 of the inner flow path that is an annular gap between the outer peripheral surface of the tip connection portion 19 and an inner peripheral surface of the front end side collar 31, and the discharge port 95 of the outer flow path that is an arc-shaped gap between a radially outer side of the glass rod 25 and the outer body 11. The cleaning liquid supplied from the central flow path FC shown in FIG. 8 is discharged from the discharge port 91, and the cleaning liquid supplied from the peripheral flow path FS is discharged from the discharge ports 93, 95.

That is, the cleaning liquid supplied from the connector portion 21 to the central connection port 41 in the central flow path FC cleans the main body side water injection flow path 43 and is discharged from the discharge port 91. The cleaning liquid supplied from the connector portion 21 to the cleaning liquid injection port 49 in the peripheral flow path FS flows between the inner peripheral surface of the outer body 11 and an outer peripheral surface of the ultrasonic vibrator 17 on an inner peripheral side and an outer peripheral side of the rear end side collar 33, passes through outside of the ultrasonic vibration source 27, flows on an inner peripheral side and an outer peripheral side of the front end side collar 31, and is discharged from the discharge ports 93, 95.

In this way, in the peripheral flow path FS, the insert body 15 disposed inside the dental handpiece 100 is immersed in the cleaning liquid, and the cleaning liquid in which the insert body 15 is immersed is discharged from the discharge ports 93, 95. Therefore, even in a case where the dental handpiece 100 is used for the treatment of the patient and a residue is generated due to intrusion of foreign matter or the like into the handpiece, the cleaning liquid flows in the handpiece in a cleaning process of the dental handpiece 100, and thus the residue may be reliably treated. In a case where an electrical component is built in the insert body 15, foreign matter including dust adhering due to, for example, static electricity may also be washed away with the cleaning liquid.

In general, since the residue is likely to adhere to a narrow gap, it is difficult to reliably remove the residue by a general method of cleaning from outside of the handpiece, and disassembly cleaning is required. However, according to the dental handpiece 100 having the above configuration, inside of the handpiece may be easily cleaned without being disassembled. That is, in a case where the inside of the handpiece is filled with the cleaning liquid, the insert body 15 is immersed in the cleaning liquid, and dirt attached to the insert body 15 floats. Then, by discharging the cleaning liquid in which the insert body 15 is immersed, the floating dirt is discharged. In addition, since the cleaning liquid flows into every corner inside the handpiece while being stirred by various types of unevenness, through holes, and the like inside the handpiece, an cleaning effect is improved by a momentum of the liquid flow. That is, the inside of the handpiece has an uneven structure using a large number of engagement portions (claw portions and receiving portions) having the snap-fit structure in addition to the through holes, the protrusions, and the grooves of the respective portions of the insert body 15. As a result, an effect of treating the residue by the cleaning liquid is improved.

In the dental handpiece 100, since the flow path of the cleaning liquid is a flow path along one direction, the cleaning liquid is smoothly discharged from the inside of the handpiece to the outside, and liquid accumulation inside the handpiece is less likely to occur.

The ultrasonic vibration source 27, which is an electrical component disposed inside the handpiece, is liquid-tightly covered with the elastic cover 45, thereby preventing water from entering inside of the electrical component. Since the elastic cover 45 has insulating properties and chemical resistance, the electrical component is protected from the cleaning process. Therefore, even in a case where the inside of the handpiece is filled with the cleaning liquid, the electric component is not affected.

According to the above configuration, a high cleaning effect may be obtained without complicating the cleaning process, and determination of a guideline for a dental handpiece cleaning process defined in each country may be reliably cleared.

<Cleaning Adapter>

Next, the cleaning adapter 200 will be described.

As shown in FIG. 1, the cleaning adapter 200 is configured to be connected to the rear end portion of the dental handpiece 100, and supply the cleaning liquid to the dental handpiece 100. In general, the dental handpiece 100 is connectable to a cleaning device that includes various external devices for cleaning and disinfecting the handpiece, and a user of the dental handpiece connects the dental handpiece to the cleaning device via a cleaning adapter corresponding to the dental handpiece to perform cleaning and disinfecting treatment.

(First Configuration Example of Cleaning Adapter)

Figure 14:
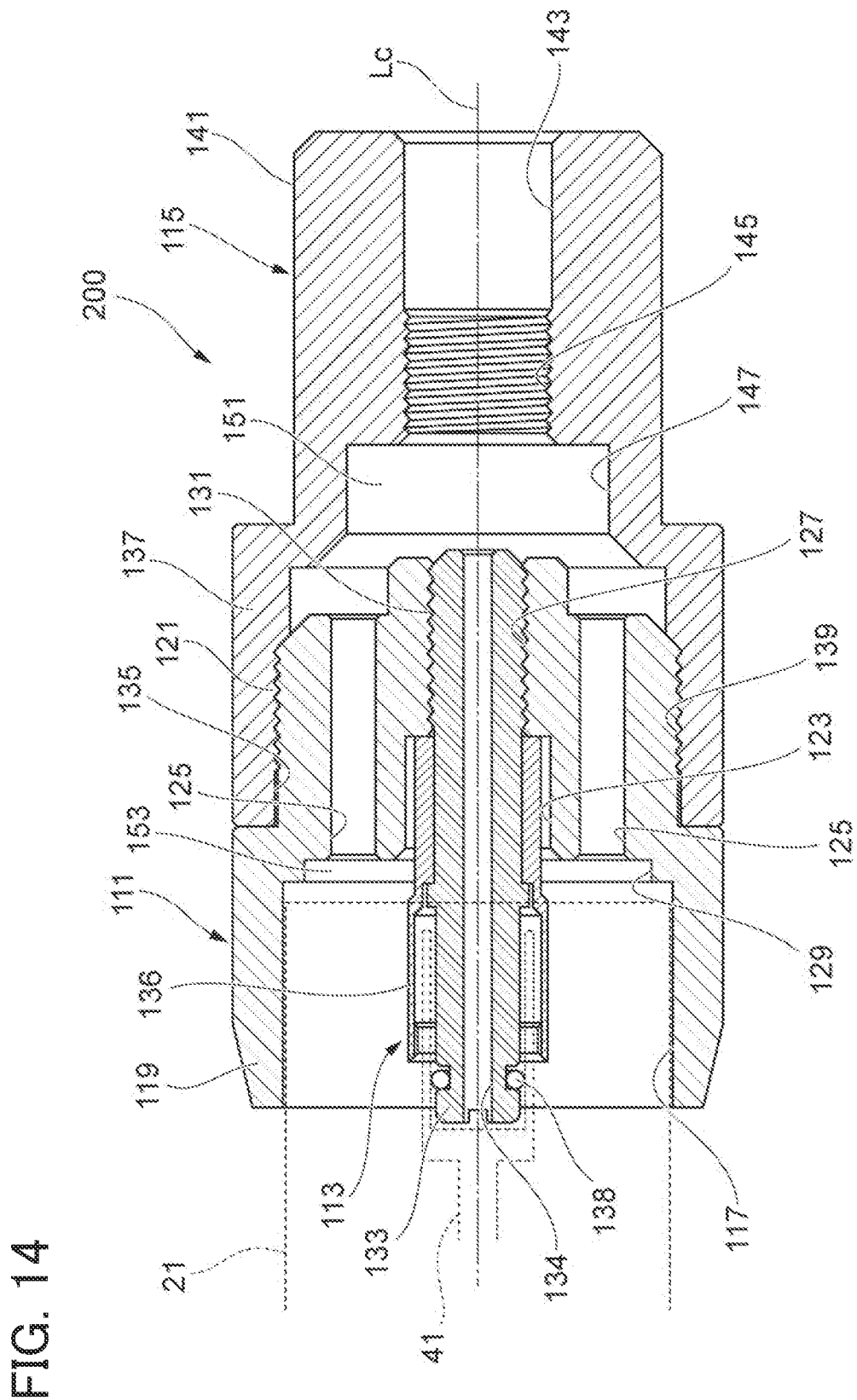
FIG. 14 is a cross-sectional view showing the cleaning adapter according to a first configuration example.
Figure 15:
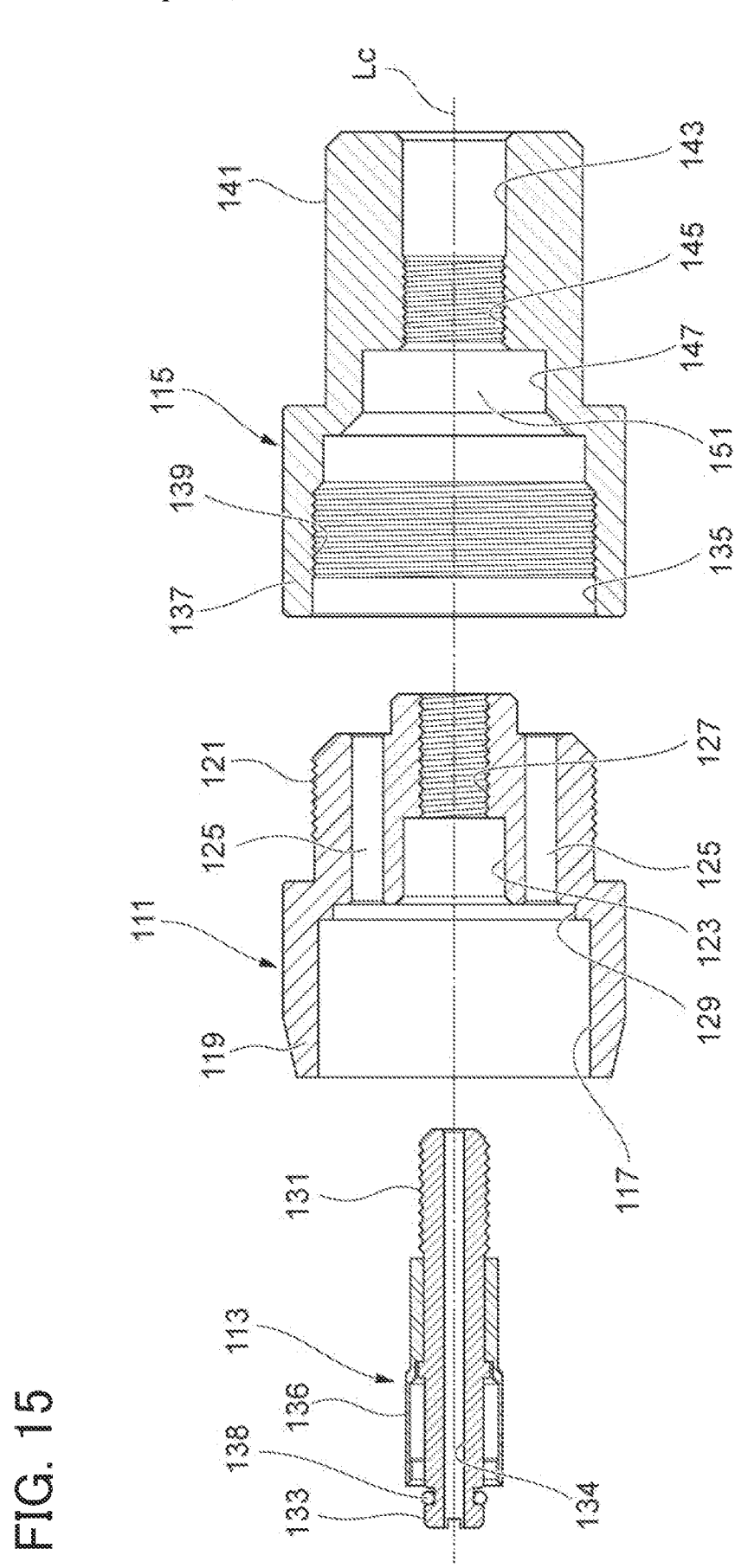
FIG. 15 is an exploded view of the cleaning adapter shown in FIG. 14.
Figure 16:
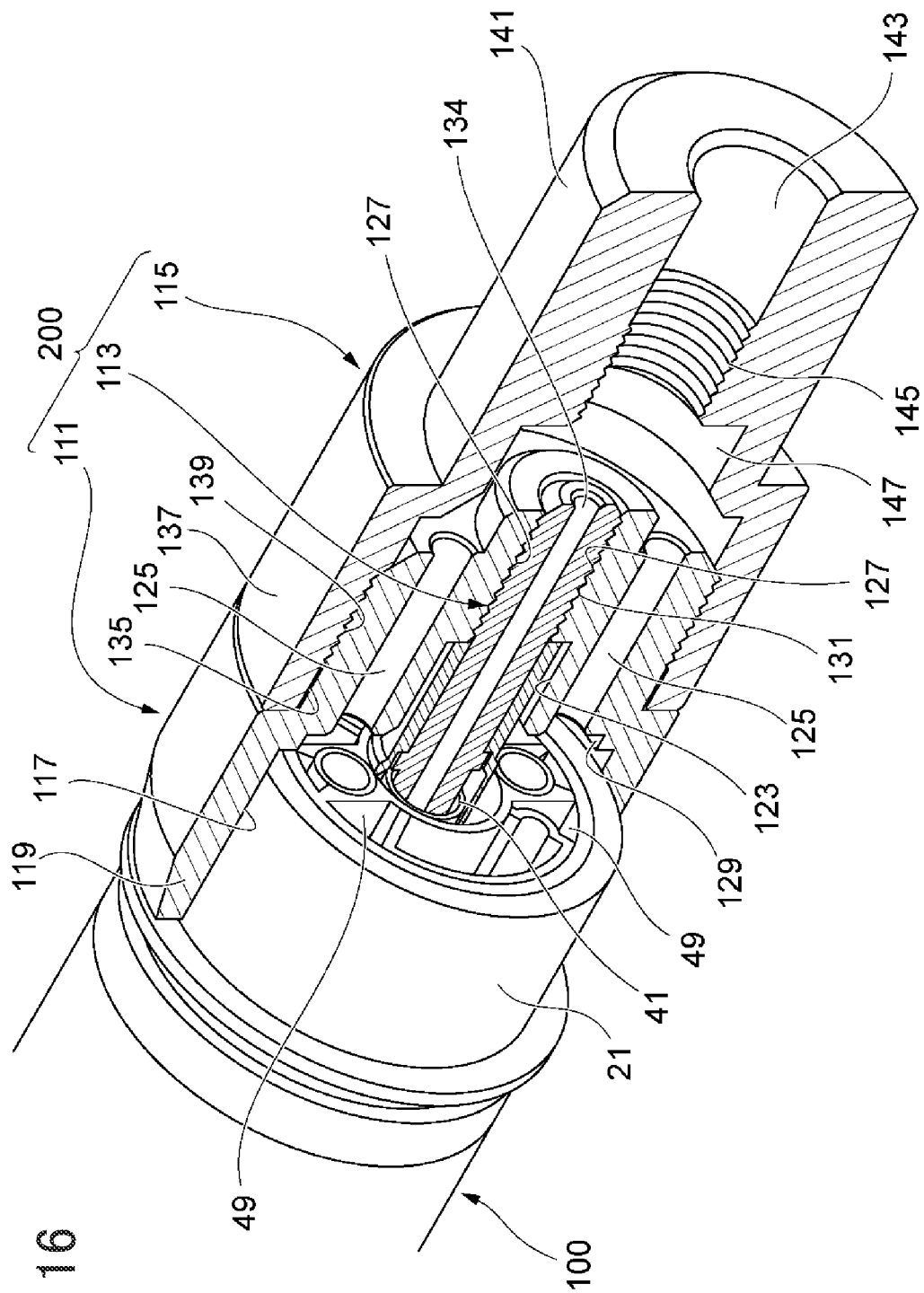
FIG. 16 is a partial cross-sectional perspective view showing a connection state between the cleaning adapter and the dental handpiece.
Figure 17:
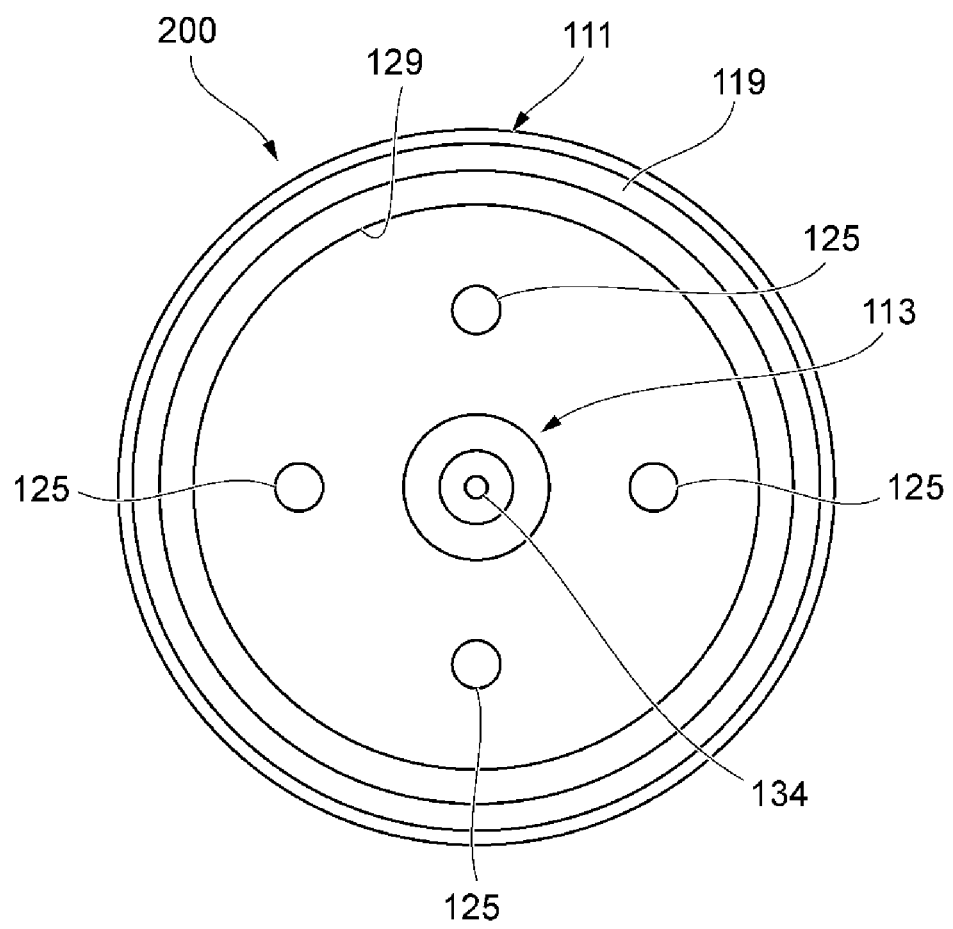
FIG. 17 is an end view of the cleaning adapter on the front end side.

FIG. 14 is a cross-sectional view showing the cleaning adapter 200 according to a first configuration example. FIG. 15 is an exploded view of the cleaning adapter 200 shown in FIG. 14. FIG. 16 is a partial cross-sectional perspective view showing a connection state between the cleaning adapter 200 and the dental handpiece 100. FIG. 17 is an end view of the cleaning adapter 200 on the front end side.

As shown in FIGS. 14 and 15, the cleaning adapter 200 includes a connector main body 111, a water injection flow path connection portion 113, and a cleaning device connection portion 115. As shown in FIG. 16, the connector main body 111 includes a flange portion 119 that forms a recess 117 on the front end side. The flange portion 119 is fitted to an outer peripheral surface of the connector portion 21 and is connected to the dental handpiece 100. A male screw 121 that fixes the cleaning device connection portion 115 is formed on an outer peripheral surface of the connector main body 111 on the rear end side. The connector body 111 is provided with a through hole 123 along a central axis Lc shown in FIG. 14 and a plurality of peripheral holes 125 on a radially outer side around the through hole 123. A female screw 127 is formed on an inner peripheral surface of the through hole 123. A counterbore portion 129 having a diameter smaller than that of an inner peripheral surface of the flange portion 119 is formed on a bottom surface of the recess 117, and a plurality of peripheral holes 125 are opened in the counterbore portion 129.

As shown in FIG. 17, the plurality of peripheral holes 125 are provided at, for example, four positions at equal intervals in the circumferential direction, but the number of peripheral holes 125 is not limited thereto.

The water injection flow path connection portion 113 is disposed on the central axis Lc of the connector main body 111 shown in FIG. 14, and a male screw 131 formed on the rear end side is fastened to the female screw 127 of the connector main body 111. A connection end 133 of the water injection flow path connection portion 113 on the front end side protrudes from the bottom surface of the recess 117 and is connected to the central connection port 41 of the dental handpiece 100 (see FIG. 16). A through hole 134 penetrating along the axial direction is formed in the water injection flow path connection portion 113.

A plurality of thin flexible springs 136 obtained by dividing a thin cylindrical body by slits in the axial direction are provided on an outer periphery of the connection end 133. The thin flexible spring 136 presses the central connection port 41 inserted into the connection end 133 from the outside to the inside by its own elasticity to sandwich the central connection port 41. The thin flexible spring 136 improves sealability between the connection end 133 and the central connection port 41. An O-ring 138 is disposed on an outer peripheral surface of a front end of the connection end 133. The O-ring 138 is pressed against an inner peripheral surface of the central connection port 41 to improve liquid tightness. At the same time, a frictional force is generated in an insertion/removal direction of the central connection port 41. This frictional force prevents the dental handpiece 100 from falling off due to a pressure of the cleaning liquid during cleaning. In this way, a connection structure between the water injection flow path connection portion 113 and the central connection port 41 may more stably hold the dental handpiece 100 while withstanding an internal pressure of the cleaning liquid.

As shown in FIG. 15, the cleaning device connection portion 115 has a flange portion 137 that forms a recess 135 on the front end side. A female screw 139 to be fastened to the male screw 121 of the connector main body 111 shown in FIG. 14 is formed on an inner peripheral surface of the flange portion 137. A shaft portion 141 connected to the cleaning device is provided on a rear end side of the cleaning device connection portion 115. A through hole 143 is provided in the shaft portion 141 along the central axis Lc, and a female screw 145 is formed on an inner peripheral surface of the through hole 143. A counterbore portion 147 is formed between the recess 135 and the through hole 143.

In the cleaning adapter 200 having the above configuration, as shown in FIG. 14, a space serving as a liquid injection side storage portion 151 is defined on the rear end side between the counterbore portion 147 communicating with the through hole 143 and the connector main body 111. In the liquid injection side storage portion 151, rear ends of the plurality of peripheral holes 125 and a rear end of the through hole 134 of the water injection flow path connection portion 113 are both opened. The counterbore portion 129 communicating with the plurality of peripheral boles 125 is formed on a connection side of the connector main body 111 to the connector portion 21. A liquid delivery side storage portion 153 is defined between the counterbore portion 129 and the connector portion 21. The liquid delivery side storage portion 153 does not communicate with the through hole 134 of the water injection flow path connection portion 113.

(Connection to Cleaning Device)

Next, a flow of the cleaning liquid when connected to the cleaning adapter 200 and the cleaning device having the above configuration will be described.

Examples of a connection form with the cleaning device include the following forms.

(1) The cleaning adapter 200 is connected to a nozzle of a spray can (for example, WL-clean manufactured by ALPRO MEDICAL GmbH) that store a cleaning liquid or a nozzle of a spray gun that sprays a cleaning liquid. The cleaning liquid may by disinfectant or dry air.

(2) The cleaning adapter 200 is connected to a handpiece holder that holds a handpiece and supplies a cleaning liquid to inside of the handpiece in a hot water cleaner in which the handpiece is disposed in a sealed cleaning container and the cleaning liquid flows into the disposed bandpiece. For example, the hot water cleaner may be SOKUSEN which is a registered trademark by Takara Belmont.

(3) A dedicated cleaning adapter is connected to an autoclave device dedicated to a handpiece. For example, the autoclave device may be DAC UNIVERSAL 2 GUI manufactured by Dentsply Sirona.

Figure 18:
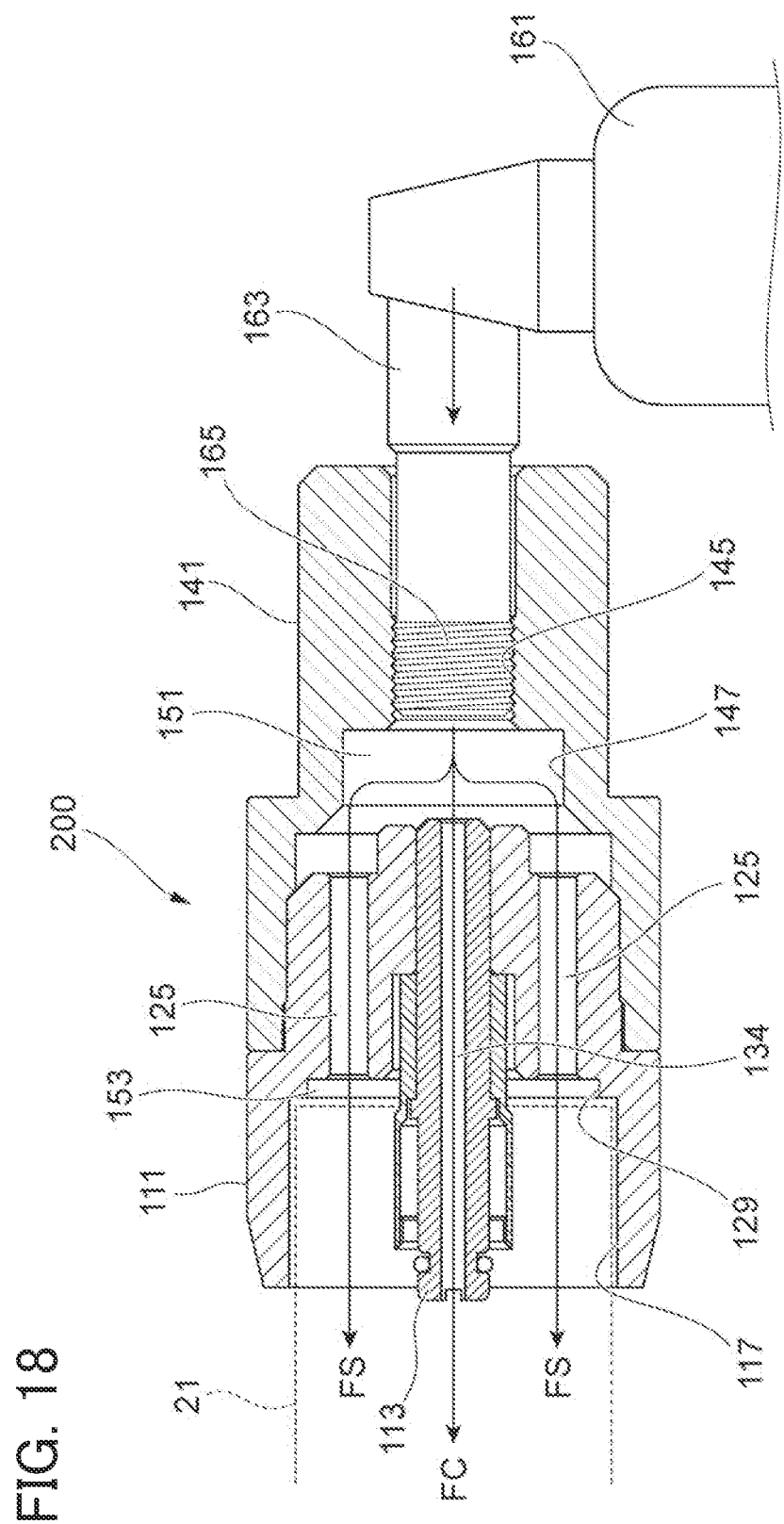
FIG. 18 is an explanatory view showing a state in which the cleaning adapter is connected to a nozzle of a spray can.

FIG. 18 is an explanatory view showing a state in which the cleaning adapter 200 is connected to a nozzle of a spray can.

In a case of the above (1), a nozzle attachment 163 is attached to a spray port of a spray can 161. A male screw 165 that may be fastened to the female screw 145 of the cleaning adapter 200 is formed at a front end of the nozzle attachment 163. The nozzle attachment 163 is attached to the cleaning adapter 200 by fastening the male screw 165 to the female screw 145.

Then, in a case where the cleaning liquid is sprayed from the spray can 161, the cleaning liquid is supplied to the liquid injection side storage portion 151. The liquid injection side storage portion 151 is filled with the supplied cleaning liquid, and the cleaning liquid is sent from the liquid injection side storage portion 151 to the main body side water injection flow path 43 (see FIG. 8) through the through hole 134 of the water injection flow path connection portion 113. This flow path serves as the central flow path FC described above.

The cleaning liquid is sent from the liquid injection side storage portion 151 to the cleaning liquid injection port 49 (see FIG. 8) through the plurality of peripheral holes 125. This flow path serves as the peripheral flow path FS described above. Here, the cleaning liquid that has passed through openings of the peripheral holes 125 on the front end side is temporarily accumulated in the liquid delivery side storage portion 153. The liquid delivery side storage portion 153 is a sealed space between a rear end of the connector part 21 connected to the recess 117 and the counterbore portion 129, and may stably supply the cleaning liquid to the cleaning liquid injection port 49 of the connector portion 21 by an internal pressure of the cleaning liquid filled in this space.

Even in a case where circumferential positions of the peripheral holes 125 and the cleaning liquid injection port 49 do not overlap with each other and are shifted from each other, the liquid delivery side storage portion 153 may uniformly supply the cleaning liquid from each cleaning liquid injection port 49. A supply amount of the cleaning liquid may be easily increased.

Figure 19:
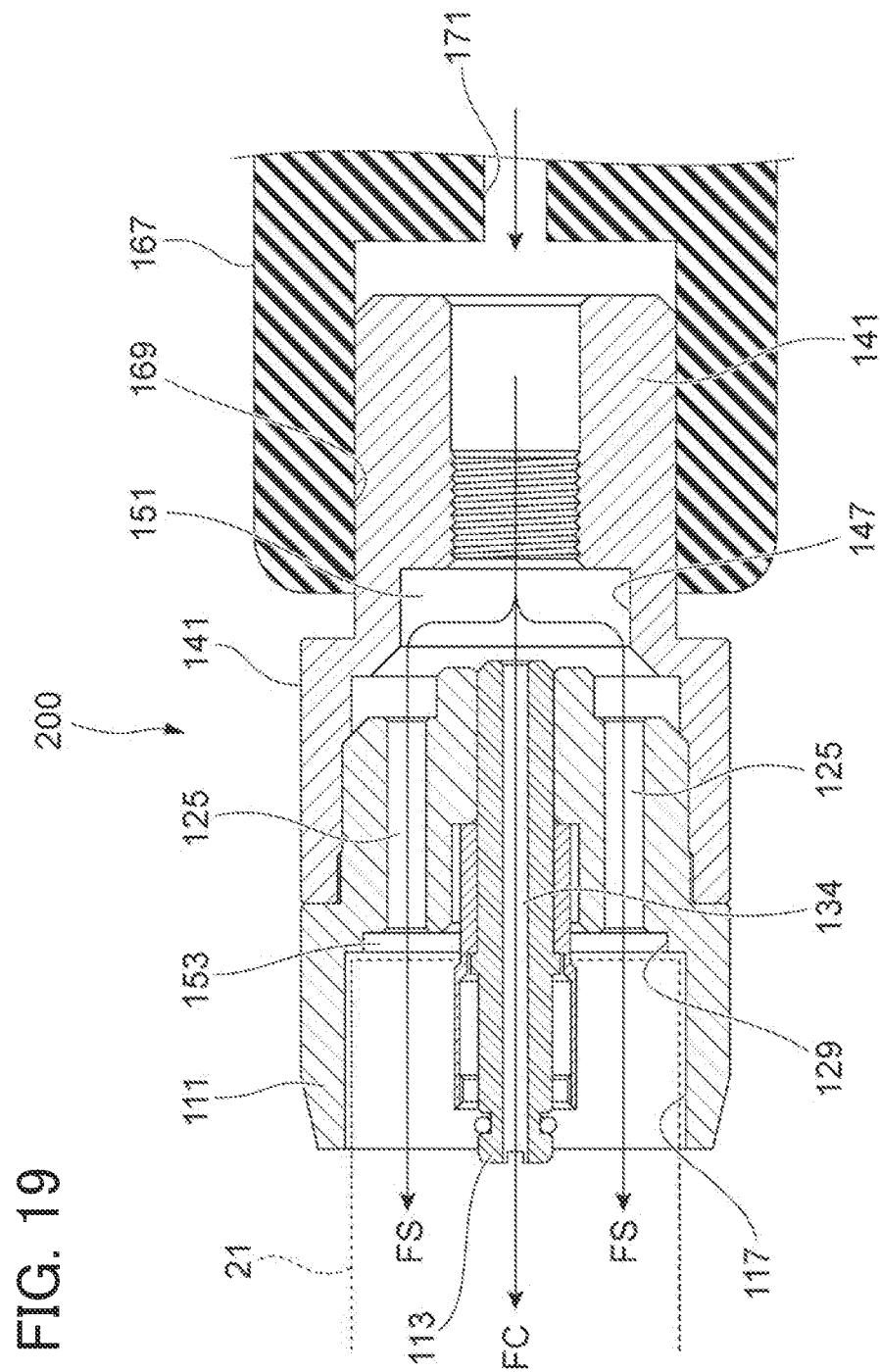
FIG. 19 is an explanatory view showing a state in which the cleaning adapter is connected to a handpiece holder of a hot water cleaner.

FIG. 19 is an explanatory view showing a state in which the cleaning adapter 200 is connected to a handpiece holder 167 of a hot water cleaner.

The handpiece bolder 167 of the hot water cleaner is a flexible elastic body including silicon rubber, and the cleaning liquid is supplied from a cleaning liquid supply port 171 at a bottom portion of a holder recess 169.

In a case of the above (2), the dental handpiece may be fixed to the hot water cleaner by a simple operation of merely inserting the shaft portion 141 of the cleaning adapter 200 into the holder recess 169. A flow of the cleaning liquid in this case is the same as that in a case of FIG. 18 described above.

(Second Configuration Example of Cleaning Adapter)

Figure 20:
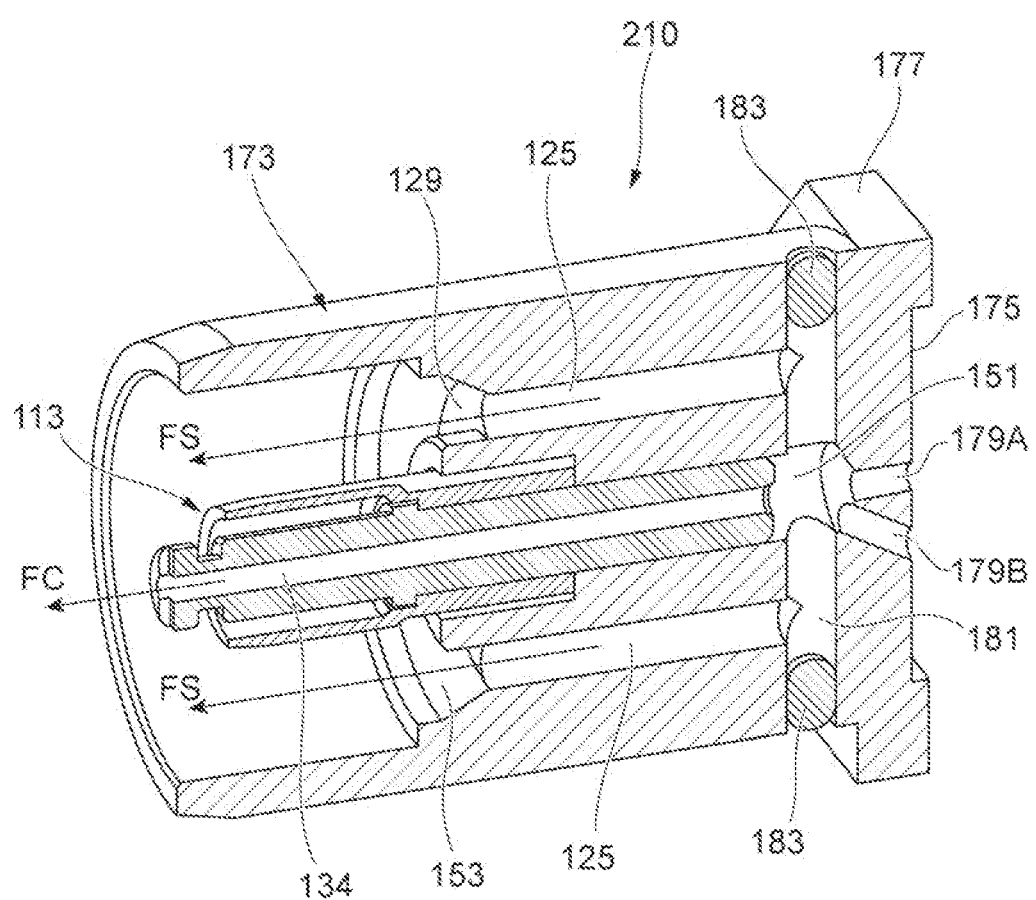
FIG. 20 is a cross-sectional view showing a configuration of the cleaning adapter connected to an autoclave device dedicated to a handpiece.

FIG. 20 is a cross-sectional view showing a configuration of a cleaning adapter 210 connected to an autoclave device dedicated to a handpiece.

The cleaning adapter 210 in a case of the above (3) is different from a structure in which the connector main body 111 and the cleaning device connection portion 115 shown in FIG. 14 are separated from each other, and includes a connector main body 173 and the water injection flow path connection portion 113.

A pedestal 177 having a groove 175 to be fixed to the autoclave device is provided at a rear end of the connector main body 173. Injection holes 179A, 179B into which the cleaning liquid is injected are formed in a bottom surface of the groove 175, and one of the injection holes 179A, 179B is selectively used depending on a type of the autoclave device. Front end side of the injection holes 179A, 179B are connected to a through hole 181 communicating with the plurality of peripheral holes 125 and the through hole 134 of the water injection flow path connection portion 113. Both end portions of the through hole 181 are closed by appropriate plug bodies 183 to define a space serving as the liquid injection side storage portion 151 described above.

According to the cleaning adapter 210, the cleaning liquid injected from one of the injection holes 179A, 179B is sent to the main body side water injection flow path 43 through the through hole 134 (see FIG. 8) and is supplied to the central flow path FC. The cleaning liquid is sent to the cleaning liquid injection port 49 through the peripheral holes 125 (see FIG. 8), and is sent to the peripheral flow path FS. A space serving as the liquid delivery side storage portion 153 is defined on the front end side of the peripheral boles 125, and the cleaning liquid may be stably supplied to the cleaning liquid injection port 49.

The present disclosure is not limited to the embodiment described above, and modifications, improvements, and the like may be made as appropriate. In addition, materials, shapes, sizes, numerical values, forms, numbers, arrangement positions, and the like of components in the embodiment described above are optional and are not limited as long as the present disclosure may be achieved.

As described above, the following matters are disclosed in the present specification.

(1) A dental handpiece comprising:
a cylindrical outer body;
an insert body that is configured to include an ultrasonic vibrator, and is accommodated in the outer body with a front end portion thereof closing a case front end of the outer body and a rear end portion thereof closing a case rear end of the outer body;
a tip connection portion that is provided at the front end portion of the insert body and that detachably holds a scale tip to which ultrasonic vibration from the ultrasonic vibrator is transmitted; and a cleaning liquid flow path that guides a cleaning liquid supplied from a cleaning liquid injection port provided in the rear end portion of the insert body to a front end portion of the outer body, wherein the cleaning liquid flow path includes an immersion flow path in which the insert body is immersed in the cleaning liquid in the outer body and the cleaning liquid in which the insert body is immersed is discharged from the front end portion of the outer body.

According to this dental handpiece, the insert body is immersed in the cleaning liquid supplied from a connector portion in the outer body, and the cleaning liquid in which the insert body is immersed is discharged from the front end portion of the outer body. Therefore, a residue accumulated in the outer body may be reliably treated with the cleaning liquid without disassembling the dental handpiece.

(2) The dental handpiece according to (1), further comprising:

a housing member that is disposed inside the outer body and covers an outer side of the ultrasonic vibrator, wherein the immersion flow path includes an inner flow path between the insert body and the housing member and an outer flow path between the housing member and the outer body.

According to this dental handpiece, the cleaning liquid flows in each of the inner flow path and the outer flow path of the housing member in the outer body, whereby the cleaning liquid is stirred, and dirt in the outer body may be efficiently treated.

(3) The dental handpiece according to (2), wherein the housing member is provided with a through hole that allows the inner flow path and the outer flow path to communicate with each other.

According to this dental handpiece, since the cleaning liquid flows from inside to outside and from the outside to the inside of the housing member through the through hole, the cleaning liquid may flow over the entire housing member, and stagnation is less likely to occur.

(4) The dental handpiece according to (2) or (3), wherein at least one of an inner peripheral surface and an outer peripheral surface of the housing member is provided with a protrusion protruding in a thickness direction of the housing member or a recess recessed in the thickness direction.

According to this dental handpiece, an effect of stirring the cleaning liquid is enhanced by the protrusion or the recess.

(5) The dental handpiece according to any one of (2) to (4), wherein the ultrasonic vibrator includes an ultrasonic vibration source and a vibration transmission member that transmits ultrasonic vibration generated from the ultrasonic vibration source to the scaler tip, and wherein the housing member includes a front end side collar that covers a region from the ultrasonic vibration source to a front end portion of the vibration transmission member, and a rear end side collar that covers a region from the ultrasonic vibration source to the cleaning liquid injection port and has an injection port for the cleaning liquid to be supplied to the cleaning liquid flow path.

According to this dental handpiece, a flow path of the cleaning liquid is formed along the front end side collar and the rear end side collar.

(6) The dental handpiece according to (5), wherein at least one of the front end side collar and the rear end side collar is formed of a pair of collar half bodies each having a half cylindrical shape, and includes an engagement portion in which a claw portion provided in one collar half body and a receiving portion provided in the other collar half body are engaged with each other in a case where the half collar bodies are combined with each other.

According to this dental handpiece, the effect of stirring the cleaning liquid is enhanced by unevenness formed by the claw portion and the receiving portion of the engagement portion.

(7) The dental handpiece according to (6), wherein the claw portion is formed so as to be surrounded by a slit formed in the collar half body.

According to this dental handpiece, since the claw portion is formed by being surrounded by the slit, a through hole is formed around the claw portion. The cleaning liquid flows to the inside and the outside of the housing member through the through hole.

(8) The dental handpiece according to any one of (2) to (7), wherein the immersion flow path includes:

a flow path reduction portion in which a flow path cross-sectional area of the outer flow path gradually decreases from the rear end portion side toward the front end portion side of the outer body;

a flow path regulation portion that regulates a part of a flow of the cleaning liquid in the outer flow path by bringing the housing member and a part of the outer body into contact with each other at a front end of the flow path reduction portion, and a flow path enlargement portion in which a flow path cross-sectional area of the outer flow path gradually increases from the flow path regulation portion toward the front end portion side.

According to this dental handpiece, stirring of the cleaning liquid is promoted by reduction and enlargement of the flow path cross-sectional area due to the outer flow path of the cleaning liquid being narrowed by the flow path reduction portion, a part of the flow path being regulated by the flow path regulation portion, and the outer flow path being widened by the flow path enlargement portion.

(9) The dental handpiece according to (8), further comprising:

a flow path re-reduction portion in which a flow path cross-sectional area of the outer flow path gradually decreases from the flow path enlargement portion toward the front end portion side; and an outer flow path regulation portion that regulates a part of the flow in the outer flow path by bringing the housing member and a part of the outer body into contact with each other on the front end portion side of the flow path re-reduction portion, wherein the cleaning liquid from the inner flow path and the outer flow path is respectively discharged from mutually different discharge ports around the tip connection portion.

According to this dental handpiece, a part of the cleaning liquid in the outer flow path passing through the re-reduction portion is regulated by the outer flow path regulation portion, whereby the cleaning liquid is stirred in a turbulent flow on the front end portion side having the largest amount of residue, and the cleaning liquid is discharged from a discharge port of the outer flow path.

(10) The dental handpiece according to any one of (1) to (9), wherein the cleaning liquid flow path includes a main body side water injection flow path connected to a tip side water injection flow path of the scaler tip through a through hole along a central axis of the insert body.

According to this dental handpiece, inside of the main body side water injection flow path may be cleaned by the cleaning liquid flowing through the main body side water injection flow path.

(11) A dental handpiece with a cleaning adapter comprising:
the dental handpiece according to the configuration (10); and
a cleaning adapter that is detachably connectable to a rear end of the dental handpiece and injects the cleaning liquid supplied from an external device into the immersion flow path and the main body side water injection flow path.

According to the dental handpiece with the cleaning adapter, the cleaning liquid from the external device may be supplied to the immersion flow path and the main body side water injection flow path.

(12) The dental handpiece with the cleaning adapter according to (11),
wherein the cleaning adapter includes:
an external connection portion that is connected to the external device that supplies the cleaning liquid;
a liquid injection side storage portion that stores the cleaning liquid supplied from the external connection portion;
a central flow path that communicates with the liquid injection side storage portion and is connected to the main body side water injection flow path of the dental handpiece; and
a plurality of peripheral flow paths that communicate with the liquid injection side storage portion and are connected to the immersion flow path of the dental handpiece.

According to the dental handpiece with the cleaning adapter, the cleaning liquid from the external connection portion may be stably injected into both the central flow path and the peripheral flow paths through the liquid injection side storage portion.

(13) The dental handpiece with the cleaning adapter according to (11),
wherein the cleaning adapter includes:
an external connection portion that is connected to the external device that supplies the cleaning liquid;
a central flow path that is connected to the main body side water injection flow path of the dental handpiece and a plurality of peripheral flow paths that are connected to the immersion flow path of the dental handpiece, both communicating with the external connection portion; and
a liquid delivery side storage portion that is provided between the plurality of peripheral flow paths and the immersion flow path of the dental handpiece, stores the cleaning liquid sent from the plurality of peripheral flow paths and supplies the cleaning liquid to the immersion flow path.

According to the dental handpiece with the cleaning adapter, the cleaning liquid supplied from the plurality of peripheral flow paths is accumulated in a liquid delivery and diffusion portion, and the cleaning liquid is supplied to the immersion flow path by an internal pressure of the cleaning liquid filled in the liquid delivery and diffusion portion. Therefore, the cleaning liquid may be stably supplied to the immersion flow path regardless of formation positions of the plurality of peripheral flow paths.

(14) The dental handpiece with the cleaning adapter according to (12) or (13),
wherein the external connection portion includes a recess communicating with the central flow path and the peripheral flow paths, and
wherein a female screw connected to a cleaning liquid supply port of the external device is formed on an inner peripheral surface of the recess.

According to the dental handpiece with the cleaning adapter, the female screw is fastened to a male screw of the cleaning liquid supply port of the external device, and the cleaning liquid may be sent from the external device to a dental handpiece side.

(15) The dental handpiece with the cleaning adapter according to (12) or (13),
wherein the external connection portion includes a cylindrical protrusion protruding in an axial direction, and
wherein inside of the cylindrical protrusion communicates with the central flow path and the peripheral flow paths.

According to the dental handpiece with the cleaning adapter, by inserting the cylindrical protrusion into a holder recess of a handpiece holder including the cleaning liquid supply port of the external device, an inner peripheral surface of the handpiece holder and an outer peripheral surface of the cylindrical protrusion are brought into close contact with each other, and the cleaning liquid may be sent from the external device to the dental handpiece side.

(16) The dental handpiece with the cleaning adapter according to (12) or (13),
wherein the external connection portion includes a cleaning liquid injection hole communicating with the central flow path and the peripheral flow paths, and
wherein an outer opening of the cleaning liquid injection hole is formed in a groove bottom surface of a groove to be engaged with the external device.

According to the dental handpiece with the cleaning adapter, the cleaning liquid may be sent from the external device to the dental handpiece side through the cleaning liquid injection hole in a state where the groove of the external connection portion is engaged with the external device.

What is claimed is:
1. A dental handpiece comprising:
a cylindrical outer body;
an insert body that includes an ultrasonic vibrator, and is configured to be accommodated in the outer body, a front end portion of the insert body closing a front end of the outer body and a rear end portion of the insert body closing a rear end of the outer body;
a tip connection portion that is provided at the front end portion of the insert body and that detachably holds a scale tip to which ultrasonic vibration from the ultrasonic vibrator is transmitted;
a cleaning liquid flow path that guides a cleaning liquid supplied from a cleaning liquid injection port of the insert body to a front end portion of the outer body; and
a housing member that is disposed inside the outer body and covers an outer side of the ultrasonic vibrator,
wherein the cleaning liquid flow path includes an immersion flow path in which the insert body is immersed in the cleaning liquid in the outer body and the cleaning liquid in which the insert body is immersed is discharged from the front end portion of the outer body, and the immersion flow path includes an inner flow path between the insert body and the housing member and an outer flow path between the housing member and the outer body.

2. The dental handpiece according to claim 1, wherein the housing member is provided with a through hole through which the inner flow path and the outer flow path communicate with each other.

3. The dental handpiece according to claim 1, wherein at least one of an inner peripheral surface and an outer peripheral surface of the housing member is provided with a protrusion protruding in a thickness direction of the housing member or a recess recessed in the thickness direction.

4. The dental handpiece according to claim 1, wherein the ultrasonic vibrator includes an ultrasonic vibration source and a vibration transmission member that is configured to transmits ultrasonic vibration generated by the ultrasonic vibration source to the scaler tip, and
the housing member includes a front end side collar that covers a front region from the ultrasonic vibration source to a front end portion of the vibration transmission member, and a rear end side collar that covers a rear region from the ultrasonic vibration source to the cleaning liquid injection port and has an injection port through which the cleaning liquid is supplied to the cleaning liquid flow path.

5. The dental handpiece according to claim 4, wherein at least one of the front end side collar and the rear end side collar is formed of a pair of collar half bodies each having a half cylindrical shape, and includes an engagement portion in which a claw portion provided in one collar half body and a receiving portion provided in the other collar half body are engaged with each other in a case where the half collar bodies are combined with each other.

6. The dental handpiece according to claim 5, wherein the claw portion is surrounded by a slit formed in the collar half body.

7. The dental handpiece according to claim 1, wherein the immersion flow path includes:
a flow path reduction portion in which a flow path cross-sectional area of the outer flow path gradually decreases from the rear end portion side toward the front end portion side of the outer body;
a flow path regulation portion that regulates a part of a flow of the cleaning liquid in the outer flow path by bringing the housing member and a part of the outer body into contact with each other at a front end of the flow path reduction portion, and
a flow path enlargement portion in which a flow path cross-sectional area of the outer flow path gradually increases from the flow path regulation portion toward the front end portion side.

8. The dental handpiece according to claim 7, further comprising:
a flow path re-reduction portion in which a flow path cross-sectional area of the outer flow path gradually decreases from the flow path enlargement portion toward the front end portion side; and
an outer flow path regulation portion that regulates a part of the flow in the outer flow path by bringing the housing member and a part of the outer body into contact with each other on the front end portion side of the flow path re-reduction portion,
wherein the cleaning liquid from the inner flow path and the outer flow path is respectively discharged from mutually different discharge ports around the tip connection portion.

9. The dental handpiece according to claim 1, wherein the cleaning liquid flow path includes a main body side water injection flow path connected to a tip side water injection flow path of the scaler tip through a through hole along a central axis of the insert body.

10. A dental handpiece with a cleaning adapter comprising:
the dental handpiece according to claim 9; and
a cleaning adapter that is configured to be detachably connected to a rear end of the dental handpiece and guide the cleaning liquid supplied from an external device into the immersion flow path and the main body side water injection flow path.

11. The dental handpiece with the cleaning adapter according to claim 10, wherein the cleaning adapter includes:
an external connection portion that is configured to be connected to the external device that supplies the cleaning liquid;
a liquid injection side storage portion that is configured to store the cleaning liquid supplied from the external connection portion;
a central flow path that communicates with the liquid injection side storage portion and is configured to be connected to the main body side water injection flow path of the dental handpiece; and
a plurality of peripheral flow paths that communicate with the liquid injection side storage portion and are configured to be connected to the immersion flow path of the dental handpiece.

12. The dental handpiece with the cleaning adapter according to claim 11, wherein the external connection portion includes a recess communicating with the central flow path and the peripheral flow paths, and
wherein a female screw connected to a cleaning liquid supply port of the external device is formed on an inner peripheral surface of the recess.

13. The dental handpiece with the cleaning adapter according to claim 11, wherein the external connection portion includes a cylindrical protrusion protruding in an axial direction, and
wherein inside of the cylindrical protrusion communicates with the central flow path and the peripheral flow paths.

14. The dental handpiece with the cleaning adapter according to claim 11, wherein the external connection portion includes a cleaning liquid injection hole communicating with the central flow path and the peripheral flow paths, and
wherein an outer opening of the cleaning liquid injection hole is formed in a groove bottom surface of a groove to be engaged with the external device.

15. The dental handpiece with the cleaning adapter according to claim 10, wherein the cleaning adapter includes:
an external connection portion that is configured to be connected to the external device that supplies the cleaning liquid;
a central flow path that is configured to be connected to the main body side water injection flow path of the dental handpiece and a plurality of peripheral flow paths that are connected to the immersion flow path of the dental handpiece, both communicating with the external connection portion; and a liquid delivery side storage portion that is provided between the plurality of peripheral flow paths and the immersion flow path of the dental handpiece, stores the cleaning liquid sent from the plurality of peripheral flow paths and supplies the cleaning liquid to the immersion flow path.

* * * * *